US011538591B2

(12) United States Patent
Dweik

(10) Patent No.: US 11,538,591 B2
(45) Date of Patent: Dec. 27, 2022

(54) TRAINING AND REFINING FLUID MODELS USING DISPARATE AND AGGREGATED MACHINE DATA

(71) Applicant: Altair Engineering, Inc., Troy, MI (US)

(72) Inventor: Zain S. Dweik, Hamilton, OH (US)

(73) Assignee: Altair Engineering, Inc., Troy, MI (US)

( * ) Notice: Subject to any disclaimer, the term of this patent is extended or adjusted under 35 U.S.C. 154(b) by 994 days.

(21) Appl. No.: 15/630,931

(22) Filed: Jun. 22, 2017

(65) Prior Publication Data

US 2018/0259978 A1 Sep. 13, 2018

Related U.S. Application Data

(60) Provisional application No. 62/469,953, filed on Mar. 10, 2017.

(51) Int. Cl.
*G06N 5/04* (2006.01)
*G16H 50/50* (2018.01)
(Continued)

(52) U.S. Cl.
CPC ......... *G16H 50/50* (2018.01); *G05B 13/0265* (2013.01); *G05B 13/041* (2013.01);
(Continued)

(58) Field of Classification Search
CPC ........ G16H 50/50; G16H 30/40; G16H 50/20; G06N 20/00; G06N 5/04; G06F 30/20;
(Continued)

(56) References Cited

U.S. PATENT DOCUMENTS 7,991,598 B1 * 8/2011 Wood .................... F16H 57/00
703/7
8,526,701 B2 9/2013 Razifar et al.
(Continued)

FOREIGN PATENT DOCUMENTS

CN 101216949 7/2008
CN 101655803 2/2010
(Continued)

OTHER PUBLICATIONS

Extended European Search Report received for EP Patent Application Serial No. 18160269.9 dated Jul. 16, 2018, 9 pages.
(Continued)

*Primary Examiner* — Alexy Shmatov
*Assistant Examiner* — Casey R. Garner
(74) *Attorney, Agent, or Firm* — Fish & Richardson P.C.

(57) ABSTRACT

A multiple fluid model tool for training and/or refining of fluid models using disparate and/or aggregated machine data is presented. For example, a system includes a modeling component, a machine learning component, a three-dimensional design component and a data collection component. The modeling component generates a three-dimensional model of a mechanical device based on a library of stored data elements. The machine learning component predicts one or more characteristics of the mechanical device based on a machine learning process associated with the three-dimensional model. The three-dimensional design component provides a three-dimensional design environment associated with the three-dimensional model. The three-dimensional design environment renders physics modeling data of the mechanical device on the three-dimensional model based on the one or more characteristics of the mechanical device. The data collection component collects machine data via a communication network to update the
(Continued)

three-dimensional model associated with the three-dimensional design environment.

20 Claims, 14 Drawing Sheets
(4 of 14 Drawing Sheet(s) Filed in Color)

(51) Int. Cl.
| | |
|---|---|
| *G06N 20/00* | (2019.01) |
| *G16H 30/40* | (2018.01) |
| *G06F 30/17* | (2020.01) |
| *G06F 30/20* | (2020.01) |
| *G06F 3/04815* | (2022.01) |
| *G05B 13/02* | (2006.01) |
| *G05B 13/04* | (2006.01) |
| *G05D 7/06* | (2006.01) |
| *G16H 50/20* | (2018.01) |
| *G01F 5/00* | (2006.01) |

(52) U.S. Cl.
CPC ......... *G05B 13/048* (2013.01); *G05D 7/0617* (2013.01); *G06F 3/04815* (2013.01); *G06F 30/17* (2020.01); *G06F 30/20* (2020.01); *G06N 5/04* (2013.01); *G06N 20/00* (2019.01); *G16H 30/40* (2018.01); *G01F 5/00* (2013.01); *G16H 50/20* (2018.01); *Y02T 90/00* (2013.01)

(58) Field of Classification Search
CPC ... G06F 30/17; G06F 19/321; G05B 13/0265; G05B 13/041; G05B 13/048; G05D 7/0617; Y02T 90/05
See application file for complete search history.

(56) References Cited

U.S. PATENT DOCUMENTS

| | | | |
|---|---|---|---|
| 8,548,828 B1 | 10/2013 | Longmire | |
| 8,970,592 B1 | 3/2015 | Petterson | |
| 9,014,485 B2 | 4/2015 | Moehrle | |
| 9,347,288 B2 | 5/2016 | Clemens et al. | |
| 9,507,754 B2 | 11/2016 | Fox et al. | |
| 9,760,690 B1 | 9/2017 | Petkov et al. | |
| 9,836,885 B1 | 12/2017 | Eraker et al. | |
| 9,916,538 B2 | 3/2018 | Zadeh et al. | |
| 10,198,550 B2 | 2/2019 | Lutich | |
| 10,237,567 B2 | 3/2019 | Nguyen et al. | |
| 10,237,587 B2 | 3/2019 | Rea Zanabria et al. | |
| 10,280,722 B2 | 5/2019 | Bello et al. | |
| 10,380,809 B2 | 8/2019 | Pereira | |
| 10,409,950 B2 | 9/2019 | Dweik | |
| 10,614,258 B1* | 4/2020 | Ng | G06F 30/20 |
| 10,650,114 B2 | 5/2020 | Dweik | |
| 10,803,211 B2 | 10/2020 | Dweik et al. | |
| 10,867,085 B2 | 12/2020 | Dweik et al. | |
| 10,963,599 B2 | 3/2021 | Dweik et al. | |
| 10,977,397 B2 | 4/2021 | Dweik et al. | |
| 11,004,568 B2 | 5/2021 | Dweik et al. | |
| 2003/0065413 A1 | 4/2003 | Liteplo et al. | |
| 2008/0129732 A1 | 6/2008 | Johnson et al. | |
| 2008/0243328 A1* | 10/2008 | Yu | G05B 23/0232 701/31.2 |
| 2009/0204245 A1* | 8/2009 | Sustaeta | G05B 13/024 700/99 |
| 2009/0259442 A1 | 10/2009 | Gandikota | |
| 2009/0312956 A1 | 12/2009 | Zombo et al. | |
| 2010/0180236 A1 | 7/2010 | Lin et al. | |
| 2010/0332373 A1 | 12/2010 | Crabtree et al. | |
| 2011/0115787 A1 | 5/2011 | Kadlec | |
| 2012/0191432 A1 | 7/2012 | Khataniar et al. | |
| 2012/0330869 A1 | 12/2012 | Durham | |
| 2013/0116996 A1 | 5/2013 | Callan | |
| 2013/0124166 A1 | 5/2013 | Clemens et al. | |
| 2013/0124176 A1 | 5/2013 | Fox et al. | |
| 2013/0339918 A1 | 12/2013 | Clark et al. | |
| 2013/0346047 A1 | 12/2013 | Fukushige et al. | |
| 2014/0005994 A1 | 1/2014 | O'Brien et al. | |
| 2014/0050406 A1 | 2/2014 | Buehler et al. | |
| 2014/0201126 A1 | 7/2014 | Zadeh et al. | |
| 2014/0207424 A1 | 7/2014 | Singh et al. | |
| 2014/0277939 A1 | 9/2014 | Ren et al. | |
| 2014/0280065 A1 | 9/2014 | Cronin et al. | |
| 2014/0281712 A1 | 9/2014 | Subbu et al. | |
| 2015/0066929 A1 | 3/2015 | Satzke et al. | |
| 2015/0068703 A1 | 3/2015 | de Bock et al. | |
| 2016/0044193 A1 | 2/2016 | Wells, II | |
| 2016/0044195 A1 | 2/2016 | Murrell et al. | |
| 2016/0235381 A1 | 8/2016 | Scanlan et al. | |
| 2016/0281494 A1 | 9/2016 | Shirdel et al. | |
| 2016/0284122 A1 | 9/2016 | Tatourian et al. | |
| 2016/0312552 A1 | 10/2016 | Early et al. | |
| 2017/0053463 A1 | 2/2017 | Pereira | |
| 2017/0169620 A1 | 6/2017 | Bleiweiss et al. | |
| 2017/0220887 A1 | 8/2017 | Fathi et al. | |
| 2017/0308800 A1 | 10/2017 | Cichon et al. | |
| 2017/0346817 A1 | 11/2017 | Gordon et al. | |
| 2017/0357828 A1 | 12/2017 | Phillips | |
| 2018/0085927 A1 | 3/2018 | Kapoor et al. | |
| 2018/0095450 A1 | 4/2018 | Lappas et al. | |
| 2018/0120813 A1 | 5/2018 | Coffman et al. | |
| 2018/0165418 A1 | 6/2018 | Swartz et al. | |
| 2018/0165604 A1 | 6/2018 | Minkin et al. | |
| 2018/0204111 A1 | 7/2018 | Zadeh et al. | |
| 2018/0239874 A1 | 8/2018 | Ingram et al. | |
| 2018/0259978 A1 | 9/2018 | Dweik | |
| 2018/0260501 A1 | 9/2018 | Dweik et al. | |
| 2018/0260502 A1 | 9/2018 | Dweik et al. | |
| 2018/0260503 A1 | 9/2018 | Dweik et al. | |
| 2018/0260513 A1 | 9/2018 | Dweik | |
| 2018/0260532 A1 | 9/2018 | Dweik et al. | |
| 2018/0330028 A1 | 11/2018 | Nutt et al. | |
| 2018/0351635 A1 | 12/2018 | Westervelt et al. | |
| 2018/0354641 A1 | 12/2018 | de Bock et al. | |
| 2018/0371874 A1 | 12/2018 | Shetty et al. | |
| 2019/0050506 A1 | 2/2019 | Umetani | |
| 2019/0114751 A1 | 4/2019 | Suzuki | |
| 2019/0244363 A1 | 8/2019 | Tan et al. | |
| 2019/0340331 A1 | 11/2019 | Dweik | |
| 2020/0250359 A1 | 8/2020 | Dweik | |
| 2021/0064801 A1 | 3/2021 | Dweik et al. | |
| 2021/0232721 A1 | 7/2021 | Dweik | |
| 2021/0232732 A1 | 7/2021 | Dweik et al. | |
| 2021/0272700 A1 | 9/2021 | Dweik et al. | |

FOREIGN PATENT DOCUMENTS

| | | | |
|---|---|---|---|
| CN | 102819861 | 12/2012 | |
| CN | 103294850 | 9/2013 | |
| CN | 103597519 | 2/2014 | |
| CN | 103809438 | 5/2014 | |
| CN | 104598675 | 5/2015 | |
| CN | 105246569 | 1/2016 | |
| TW | 201633193 | 9/2016 | |
| WO | 2016/038208 A2 | 3/2016 | |
| WO | WO-2017188858 A1 * | 11/2017 | ............ E21B 43/00 |
| WO | WO-2018117890 A1 * | 6/2018 | ............ G06N 20/00 |

OTHER PUBLICATIONS

Non-Final Office Action received for U.S. Appl. No. 15/627,105 dated Jun. 13, 2019, 16 pages.
Extended European Search Report received for EP Patent Application Serial No. 18160923.1 dated Jun. 13, 2018, 9 pages.
Non-Final Office Action received for U.S. Appl. No. 15/627,068 dated Jun. 27, 2019, 16 pages.
Non-Final Office Action received for U.S. Appl. No. 15/630,941 dated Aug. 3, 2018, 27 pages.
Final Office Action received for U.S. Appl. No. 15/630,941 dated Jan. 30, 2019, 29 pages.
Non-Final Office Action received for U.S. Appl. No. 15/630,941 dated Aug. 2, 2019, 30 pages.

(56) References Cited

OTHER PUBLICATIONS

Non-Final Office Action received for U.S. Appl. No. 15/630,939 dated Oct. 18, 2018, 20 pages.
Extended European Search Report received for EP Patent Application Serial No. 18160270.7 dated Jul. 16, 2018, 9 pages.
Non-Final Office Action received for U.S. Appl. No. 16/517,154 dated Aug. 22, 2019, 36 pages.
Communication pursuant to Article 94(3) EPC received for EP Patent Application Serial No. 18160923.1 dated Jul. 5, 2019, 6 pages.
Final Office Action received for U.S. Appl. No. 15/627,105 dated Jan. 16, 2020, 26 pages.
Non-Final Office Action received for U.S. Appl. No. 15/627,068 dated Dec. 26, 2019, 42 pages.
Final Office Action received for U.S. Appl. No. 15/630,941 dated Dec. 27, 2019, 42 pages.
Final Office Action received for U.S. Appl. No. 15/630,935 dated Feb. 4, 2020, 29 pages.
Non-Final Office Action received for U.S. Appl. No. 15/630,935 dated Aug. 30, 2019, 33 pages.
Notice of Allowance received for U.S. Appl. No. 15/627,105 dated Jun. 11, 2020, 21 pages.
Final Office Action received for U.S. Appl. No. 15/627,068 dated Jun. 10, 2020, 14 pages.
Non-Final Office Action received for U.S. Appl. No. 15/630,941 dated Jun. 23, 2020, 39 pages.
Non-Final Office Action received for U.S. Appl. No. 15/630,935 dated Aug. 5, 2020, 33 pages.
Non-Final Office Action received for U.S. Appl. No. 16/856,392 dated Jun. 11, 2020, 40 pages.
Office Action in Chinese Application No. 201810194306.3, dated Sep. 3, 2021, 16 pages (with translation).
Office Action in Chinese Application No. 201810195151.5, dated Sep. 3, 2021, 20 pages (with translation).
Office Action in U.S. Appl. No. 15/630,931, dated Jun. 22, 2021, 27 pages.
Search Report in Chinese Application No. 201810194306.3, dated Aug. 30, 2021, 2 pages.
Search Report in Chinese Application No. 201810195151.5, dated Aug. 30, 2021, 2 pages.
Cheng et al., "Mass point cloud data processing theory and technology," Shanghai Tongji University', 2014, p. 53 (with machine translation).

* cited by examiner

TRAINING AND REFINING FLUID MODELS USING DISPARATE AND AGGREGATED MACHINE DATA

CROSS-REFERENCE

This application claims priority to U.S. Provisional Patent Application No. 62/469,953, filed Mar. 10, 2017, and entitled "A MULTIPLE FLUID MODEL TOOL FOR INTERDISCIPLINARY FLUID MODELING", the entirety of which application is hereby incorporated by reference herein.

TECHNICAL FIELD

This disclosure relates generally to three dimensional modeling systems, and more specifically, to modeling of a fluid system and/or a fluid system design tool.

BACKGROUND

During a design phase of a device or product associated with a fluid system, it is often desirable to determine impact of a fluid with respect to the device or product associated with the fluid system. To determine impact of the fluid with respect to the design, numerical analysis of two dimensional (2D) data associated with computational fluid dynamics can be employed to analyze fluid flow through the device or product. For instance, a color of a 2D surface associated with the device or product can represent a degree of fluid flow. However, analyzing impact of a fluid with respect to a design of the device or product generally involves human interpretation of 2D data, which can result in human trial and error with respect to the fluid system. Moreover, human interpretation of 2D data and/or employing multiple fluid model tools to determine impact of a fluid with respect to a design of a device or product can be burdensome with respect to cost, redundancy and/or maintenance associated with the device or product.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

In accordance with an embodiment, a system includes a modeling component, a machine learning component, a three-dimensional design component, and a data collection component. The modeling component generates a three-dimensional model of a mechanical device based on a library of stored data elements. The machine learning component predicts one or more characteristics of the mechanical device based on a machine learning process associated with the three-dimensional model. The three-dimensional design component provides a three-dimensional design environment associated with the three-dimensional model. The three-dimensional design environment renders physics modeling data of the mechanical device on the three-dimensional model based on the one or more characteristics of the mechanical device. The data collection component collects machine data via a network device of a communication network to update the three-dimensional model associated with the three-dimensional design environment.

In accordance with another embodiment, a method provides for generating, by a system comprising a processor, a three-dimensional model of a mechanical device based on a library of stored data elements. The method also provides for predicting, by the system, fluid flow and physics behavior associated with the three-dimensional model based on a machine learning process associated with the three-dimensional model. Furthermore, the method provides for rendering, by the system, physics modeling data of the mechanical device within a three-dimensional design environment based on the fluid flow and the physics behavior. The method also provides for receiving, by the system, machine data via a network device of a communication network. Furthermore, the method provides for updating, by the system, the physics modeling data within the three-dimensional design environment based on the machine data.

In accordance with yet another embodiment, a computer readable storage device comprising instructions that, in response to execution, cause a system comprising a processor to perform operations, comprising: generating a three-dimensional model of a mechanical device based on a library of stored data elements, performing a first machine learning process associated with the three-dimensional model to predict one or more characteristics of the mechanical device, generating physics modeling data for the mechanical device based on the first machine learning process, receiving, via a network device of a communication network, machine data from the mechanical device, updating the physics modeling data to generate updated physics modeling data for the mechanical device based on a second machine learning process, and providing a three-dimensional design environment associated with the three-dimensional model that renders the updated physics modeling data for the mechanical device.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

The patent or application file contains at least one drawing executed in color. Copies of this patent or patent application publication with color drawings will be provided by the Office upon request and payment of the necessary fee. Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
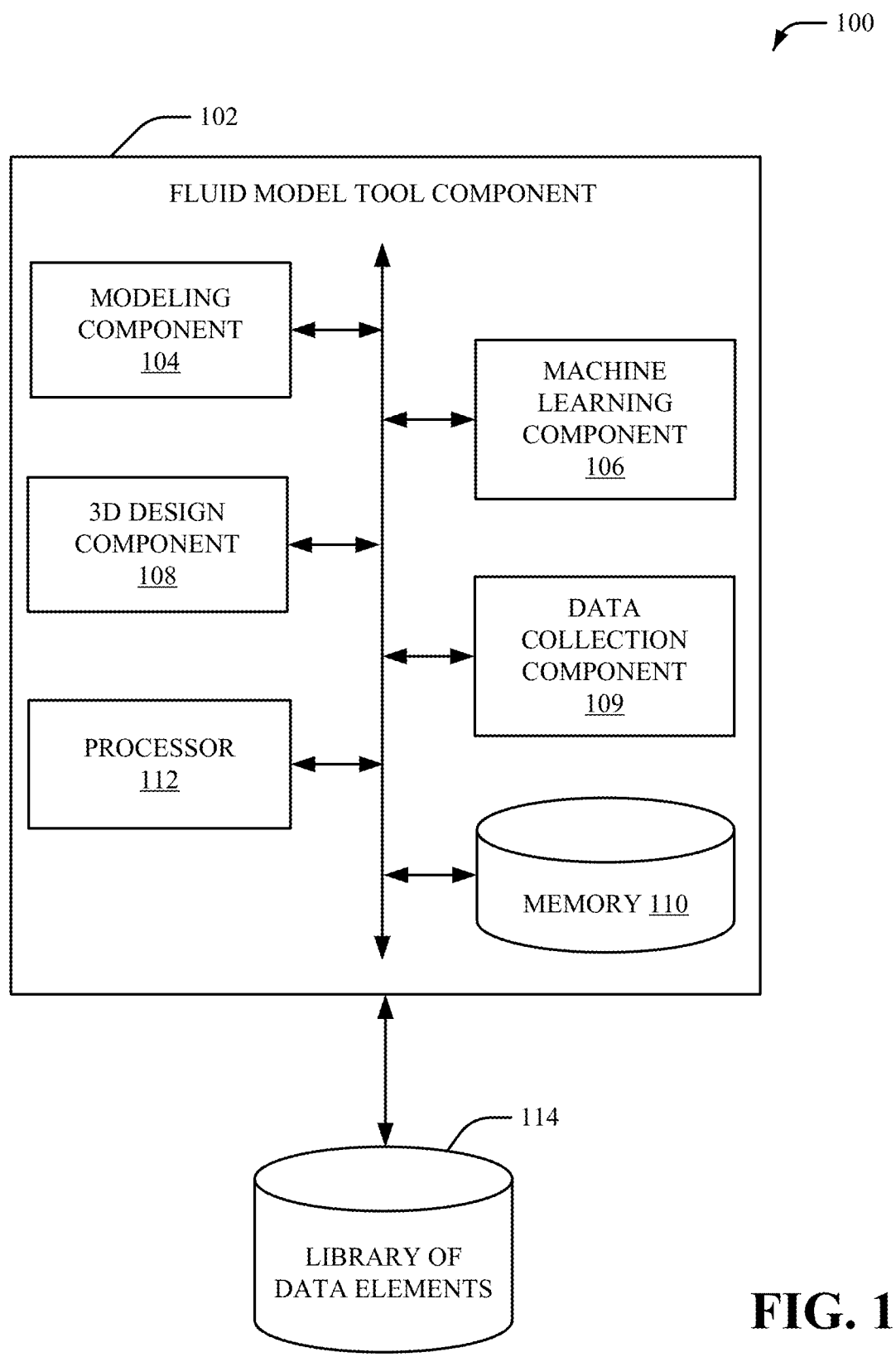
FIG. 1 illustrates a high-level block diagram of an example fluid model tool component, in accordance with various aspects and implementations described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques that facilitate training and/or refining of fluid models using disparate and/or aggregated machine data are presented. For example, as compared to conventional analysis of a fluid system that involves human interpretation of two-dimensional (2D) data and/or human trial and error with respect to a fluid system, the subject innovations provide for a three-dimensional (3D) design environment that can be generated by training and/or refining fluid models using disparate and/or aggregated machine data. In an aspect, physics modeling data associated with a degree of fluid flow can be rendered on a 3D model of a device based on disparate and/or aggregated machine data. In one example, visual characteristics of the physics modeling data can be dynamic based on the degree of fluid flow and values of the machine data. Various systems and techniques disclosed herein can be related to cloud-based services, a heating, ventilation and air conditioning (HVAC) system, a medical system, an automobile, an aircraft, a water craft, a water filtration system, a cooling system, pumps, engines, diagnostics, prognostics, optimized machine design factoring in cost of materials in real-time, explicit and/or implicit training of models through real-time aggregation of data, etc. In an embodiment, a multiple fluid model tool can provide a platform for interdisciplinary fluid modeling by training and/or refining of fluid models using disparate and/or aggregated machine data. For instance, after a machine using a 3D model is built and employed for one or more technological purposes, machine data can be collected in real-time and employed to train and/or refine the 3D model. In a non-limiting example, an automobile component (e.g., an automobile engine) can be produced based on a 3D model of the automobile component. Furthermore, machine data (e.g., engine fluid data) related to the automobile component can be transmitted by one or more vehicles associated with the automobile component to a cloud platform where the machine data is analyzed and/or employed to further train the 3D model associated with the automobile component. The updated and refined 3D model can then be employed to improve future automobile components (e.g., future engine design) and/or to regulate one or more operations associated with the automobile component (e.g., one or more maintenance operations, one or more predictive maintenance operations, one or more diagnostic operations, change of fluids related to the automobile component, use of a vehicle associated with the automobile component, etc.). In certain embodiments, live data feeds can be employed in conjunction with a set of sensors and/or a 3D design environment to provide a digital display of a status of a machine (e.g., the automobile component). Granularity of a 3D model can also facilitate isolation of problems to very fine points in a machine (e.g., a single loose fitting, etc.) based on physics modeling data. As such, a device, machine and/or component associated with a 3D model can be improved. Furthermore, a 3D model associated with physics modeling can be generated more efficiently and/or data provided by a 3D model associated with physics modeling can be more accurate. Moreover, damage to a device, machine and/or component associated with a 3D model can be minimized by replacing human trial and error for analyzing one or more characteristics associated with the 3D model of the device, machine and/or component.

Referring initially to FIG. 1, there is illustrated an example system 100 that provides for training and/or refining of fluid models using disparate and/or aggregated machine data, according to an aspect of the subject disclosure. The system 100 can be employed by various systems, such as, but not limited to modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, diagnostics systems, prognostics systems, machine design systems, medical device systems, medical imaging systems, medical modeling systems, simulation systems, enterprise systems, enterprise imaging solution systems, advanced diagnostic tool systems, image management platform systems, artificial intelligence systems, machine learning systems, neural network systems, and the like. In one example, the system 100 can be associated with a graphical user interface system to facilitate visualization and/or interpretation of 3D data. Moreover, the system 100 and/or the components of the system 100 can be employed to use hardware and/or software to solve problems that are highly technical in nature (e.g., related to processing 3D data, related to modeling 3D data, related to artificial intelligence, etc.), that are not abstract and that cannot be performed as a set of mental acts by a human.

The system 100 can include a fluid model tool component 102 that can include a modeling component 104, a machine learning component 106, a 3D design component 108 and/or a data collection component 109. In an aspect, modeling performed by the fluid model tool component 102 can be associated with a flow integrated design environment, a heat transfer design environment and/or a combustion design environment. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the fluid model tool component 102) can include memory 110 for storing computer executable components and instructions. The system 100 (e.g., the fluid model tool component 102) can further include a processor 112 to facilitate operation of the instructions (e.g., computer executable components and instructions) by the system 100 (e.g., the fluid model tool component 102). In certain embodiments, the system 100 can further include a library of data elements 114. The library of data elements 114 can be a library of stored data elements.

The modeling component 104 can generate a 3D model of a device. The 3D model can be a 3D representation of the device for presentation via a 3D design environment. In an embodiment, the modeling component 104 can generate a 3D model of a mechanical device and/or an electronic device. The modeling component 104 can generate a 3D model of a device based on, for example, the library of data elements 114. The library of data elements 114 can include a set of data elements for mechanical components and/or electrical components. Furthermore, the set of data elements can include, for example, geometry data and/or texture data. The geometry data can be indicative of a geometry of the device. In an aspect, the geometry data can include 3D data points (e.g., 3D vertices) that form a shape, a structure and/or a set of surfaces of the device via a 3D coordinate system. The geometry data can also include a set of polygons (e.g., a set of geometric faces) based on the 3D data points. In an embodiment, the geometry data can include mesh data associated with the 3D data points and/or the set of polygons. In another embodiment, the geometry data can include non-uniform rational basis spline (NURBS) data. The NURBS data can include NURBS surface data that represents a surface and/or a geometric shape of the 3D model based on a set of parameters that map surfaces in 3D coordinate system. The NURBS data can also include a set of control points that form a shape of a surface associated with the NURBS surface data. In an non-limiting example, the library of data elements 114 can include a data element for fluid source, a fuel source, flow elements, pipe systems, sealing systems, pressure drop components (e.g., orifices, valves, fittings, junctions, transitions, etc.), diffusers, heat exchangers, controllers, pumps, fans, compressors, cavities, vortexes and/or other components. Additionally or alternatively, the library of data elements 114 can include experimental data (e.g., experimental test data) associated with the device. For example, the library of data elements 114 can include one or more properties of the device that is determined via one or more experiments and/or one or more research processes. The one or more experiments and/or one or more research processes can include determining and/or capturing the one or more properties via a physical representation of the device associated with the 3D model. The one or more properties of the device can include, for example, one or more physical properties of the device, one or more mechanical properties of the device, one or more measurements of the device, one or more material properties of the device, one or more electrical properties of the device, one or more thermal properties of the device and/or one or more other properties of the device.

In certain embodiments, the modeling component 104 can perform modeling of one or more mechanical elements of a device (e.g., a mechanical device and/or an electronic device). For example, the modeling component 104 can determine a set of boundaries for features of mechanical elements of the device. Furthermore, the modeling component 104 can determine a set of physical characteristics for mechanical elements. In a non-limiting example, the modeling component 104 can determine one or more chambers of a device. The modeling component 104 can, for example, determine a set of boundaries that define the one or more chambers. The modeling component 104 can also determine a set of physical characteristics for the one or more chambers such as, for example, a size for the one or more chambers, a shape for the one or more chambers, a volume of the one or more chambers and/or another physical characteristic for the one or more chambers. In an aspect, the modeling component 104 can compute the one or more mechanical elements of the device based on the library of data elements 114. To compute the one or more mechanical elements, the modeling component 104 can employ one or more modeling techniques using the library of data elements 114. As such, the one or more mechanical elements can be one or more computationally derived elements. In another aspect, the modeling component 104 can perform a modeling process associated with the one or more modeling techniques to facilitate design of a system associated with the device, where the system includes a set of mechanical elements that are combined to form the device.

In an embodiment, the modeling component 104 can determine a set of control volumes associated with the device. For instance, the modeling component 104 can overlay a set of control volumes on the device. A control volume can be an abstraction of a region of the device through which a fluid (e.g., a liquid or a gas) and/or an electrical current flows. In one example, a control volume can correspond to a chamber of the device. The modeling component 104 can determine geometric features of the set of control volumes. For instance, the modeling component 104 can determine computational control volumes (e.g., chambers) and/or geometrical features of the computational control volumes. Control volumes can be connected via various types of preconfigured elements and/or preconfigured components to construct an analysis computational model that extends from supply to sink conditions. Control volumes can also simulate run conditions for the preconfigured elements, the preconfigured components and/or a system associated with the 3D model. The preconfigured elements and/or the preconfigured components can be included in the library of data elements 114, for example. For instance, the library of data elements 114 can include an extended library of preconfigured elements and/or preconfigured components that can be employed by the modeling component 104 to facilitate modeling and/or simulating a wide-range of physical phenomena including compressible/incompressible fluid flow, buoyancy driven flow, rotating cavity system flow, conduction/convection/radiation heat transfer, combustion equilibrium-chemistry, species transport, etc. Physical formulation of the preconfigured elements and/or the preconfigured components can be varied based on complexity of a physical phenomena to be simulated. In an aspect, physical formulation of the preconfigured elements and/or the preconfigured components can categorized as machine-learning based elements (e.g., seals, leakages, compressors, fans, junctions, bends, valves, orifices, pipes, etc.). Additionally or alternatively, physical formulation of the preconfigured elements and/or the preconfigured components can be categorized as computationally derived based elements (e.g., modeling methods utilizing a combination of analytical modeling techniques and experimental test data). Combination of the preconfigured elements and/or the preconfigured components can be employed by the modeling component 104 to construct the 3D model that can be further employed (e.g., by the machine learning component 106) to simulate and/or predict a machine steady state or transient response.

In another embodiment, the modeling component 104 can employ 3D computer-aided design (CAD) data to automatically create computational domains and/or control volumes (e.g., chambers/elements/components) for the 3D model that can be employed (e.g., by the machine learning component 106) to generate predictions for simulated machine conditions for a device associated with the 3D model. Automation of the computational model creation can significantly reduce the cycle time of analysis setup. Furthermore, computational domains can be bi-directionally linked to 3D CAD through geometric tags, CAD curves parametric expressions, surfaces parametric tags, etc. For example computational domains can be automatically updated when the CAD data is updated. In yet another embodiment, the modeling component 104 can integrate sub-components of a device (e.g., a mechanical device and/or an electronic device) and/or sub-models of a device (e.g., a mechanical device and/or an electronic device) to form, for example, sub-combinations and/or models of an entire machine. In an aspect, the modeling component 104 can integrate a first flow network of a first sub-component with a second flow network of a second sub-component. Additionally or alternatively, the modeling component 104 can integrate first heat transfer throughout a first sub-component with second heat transfer throughout a second sub-component. Additionally or alternatively, the modeling component 104 can integrate first multiphase flow through a first sub-component with second multiphase flow through a second sub-component.

The machine learning component 106 can perform learning (e.g., explicit learning and/or implicit learning) and/or can generate inferences with respect to one or more 3D models generated by the modeling component 104. The learning and/or generated inferences by the machine learning component 106 can facilitate determination of one or more characteristics associated with the one or more 3D models generated by the modeling component 104. The learning and/or generated inferences can be determined by the machine learning component 106 via one or more machine learning processes associated with the one or more 3D models. The one or more characteristics determined by the machine learning component 106 can include, for example, one or more fluid characteristics associated with the one or more 3D models generated by the modeling component 104, one or more thermal characteristics associated with the one or more 3D models generated by the modeling component 104, one or more combustion characteristics associated with the one or more 3D models generated by the modeling component 104, one or more electrical characteristics associated with the one or more 3D models generated by the modeling component 104 and/or one or more other characteristics associated with the one or more 3D models generated by the modeling component 104. In an aspect, the machine learning component 106 can predict and/or model a flow network of a mechanical element associated with the one or more 3D models, heat transfer throughout a mechanical element associated with the one or more 3D models, combustion associated with a mechanical element associated with the one or more 3D models, multiphase flow through a mechanical element associated with the one or more 3D models and/or other characteristics of a mechanical element associated with the one or more 3D models.

In an embodiment, the machine learning component 106 can predict the one or more characteristics associated with the one or more 3D models based on input data and one or more machine learning processes associated with the one or more 3D models. The input data can be, for example, a set of parameters for a fluid capable of flowing through the one or more 3D models, a set of parameters for a thermal energy capable of flowing through the one or more 3D models, a set of parameters for a combustion chemical reaction capable of flowing through the one or more 3D models, a set of parameters for electricity flowing through the one or more 3D models, and/or another set of parameters for input provided to the one or more 3D models. The one or more characteristics associated with the one or more 3D models can correspond to one or more characteristics of the device (e.g., the mechanical device and/or the electronic device). In one example, distinct types of control volumes (e.g., chambers) simulating reservoirs, volume mixing dynamics, volume inertial dynamics, volume pumping dynamics, and/or volume gravitational dynamics can be employed by the machine learning component 106 to model and/or simulate various fluid flow conditions associated with the one or more 3D models. In an aspect, the machine learning component 106 can also employ measured data and/or streamed data to set boundary conditions for one or more machine learning processes. For example, the machine learning component 106 can also employ measured data and/or streamed data to set boundary conditions for supply chambers and sink chambers and/or to establish driving forces for simulated physics phenomena (e.g., fluid dynamics, thermal dynamics, combustion dynamics, angular momentum, etc.).

Additionally or alternatively, the machine learning component 106 can perform a probabilistic based utility analysis that weighs costs and benefits related to the one or more 3D models generated by the modeling component 104. The machine learning component 106 (e.g., one or more machine learning processes performed by the machine learning component 106) can also employ an automatic classification system and/or an automatic classification process to facilitate learning and/or generating inferences with respect to the one or more 3D models generated by the modeling component 104. For example, the machine learning component 106 (e.g., one or more machine learning processes performed by the machine learning component 106) can employ a probabilistic and/or statistical-based analysis (e.g., factoring into the analysis utilities and costs) to learn and/or generate inferences with respect to the one or more 3D models generated by the modeling component 104. The machine learning component 106 (e.g., one or more machine learning processes performed by the machine learning component 106) can employ, for example, a support vector machine (SVM) classifier to learn and/or generate inferences with respect to the one or more 3D models generated by the modeling component 104. Additionally or alternatively, the machine learning component 106 (e.g., one or more machine learning processes performed by the machine learning component 106) can employ other classification techniques associated with Bayesian networks, decision trees and/or probabilistic classification models. Classifiers employed by the machine learning component 106 (e.g., one or more machine learning processes performed by the machine learning component 106) can be explicitly trained (e.g., via a generic training data) as well as implicitly trained (e.g., via receiving extrinsic information). For example, with respect to SVM's that are well understood, SVM's are configured via a learning or training phase within a classifier constructor and feature selection module. A classifier is a function that maps an input attribute vector, $x=(x1, x2, x3, x4, xn)$, to a confidence that the input belongs to a class—that is, $f(x)=confidence(class)$.

In an aspect, the machine learning component 106 can include an inference component that can further enhance automated aspects of the machine learning component 106 utilizing in part inference based schemes to facilitate learning and/or generating inferences with respect to the one or more 3D models generated by the modeling component 104. The machine learning component 106 (e.g., one or more machine learning processes performed by the machine learning component 106) can employ any suitable machine-learning based techniques, statistical-based techniques and/or probabilistic-based techniques. For example, the machine learning component 106 (e.g., one or more machine learning processes performed by the machine learning component 106) can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the machine learning component 106 (e.g., one or more machine learning processes performed by the machine learning component 106) can perform a set of machine learning computations associated with the one or more 3D models generated by the modeling component 104. For example, the machine learning component 106 (e.g., one or more machine learning processes performed by the machine learning component 106) can perform a set of clustering machine learning computations, a set of decision tree machine learning computations, a set of instance-based machine learning computations, a set of regression machine learning computations, a set of regularization machine learning computations, a set of rule learning machine learning computations, a set of Bayesian machine learning computations, a set of deep Boltzmann machine computations, a set of deep belief network computations, a set of convolution neural network computations, a set of stacked auto-encoder computations and/or a set of different machine learning computations.

In an embodiment, the machine learning component 106 can predict fluid flow and physics behavior associated with the 3D model. For instance, the machine learning component 106 can perform a machine learning process associated with fluid flow through the 3D model. The machine learning component 106 can perform the machine learning process based on input data indicative of input received by a device associated with the 3D model. For example, the input data can include fluid data indicative of a fluid provided to a device associated with the 3D model. The fluid data can include one or more properties of the fluid such as, for example, a fluid type of the fluid, a density of the fluid, a viscosity of the fluid, a volume of the fluid, a weight of the fluid, a temperature of the fluid and/or another property of the fluid. The input data can by employed by the machine learning component 106 to predict the fluid flow. The fluid flow can be, for example, fluid flow of the input data (e.g., the fluid) through the device associated with the 3D model. The physics behavior can be physics behavior of the fluid flow. For instance, the physics behavior can be simulated physics and/or changes of the fluid flow. Furthermore, the physics behavior can be simulated fluid flow conditions associated with the 3D model. The physics behavior can also include correlations and/or behavior determined based on one or more mathematical equations associated with fluid flow such as, for example, conservation equations for mass associated with a fluid, conservation equations for momentum associated with a fluid, conservation equations for energy associated with a fluid, conservation equations for angular momentum associated with a fluid, and/or another mathematical equation associated with fluid flow.

Additionally or alternatively, the machine learning component 106 can predict thermal characteristics and physics behavior associated with the 3D model. For instance, the machine learning component 106 can perform a machine learning process associated with thermal characteristics associated with the 3D model. The machine learning component 106 can perform the machine learning process based on input data indicative of input received by a device associated with the 3D model. For example, the input data can include the fluid data indicative of a fluid provided to a device associated with the 3D model. Additionally or alternatively, the input data can include electrical data indicative of a voltage and/or a current provided to a device associated with the 3D model. The input data can by employed by the machine learning component 106 to predict the thermal characteristics. The thermal characteristics can be, for example, a temperature associated with one or more regions of the 3D model, a heat capacity associated with one or more regions of the 3D model, thermal expansion associated with one or more regions of the 3D model, thermal conductivity associated with one or more regions of the 3D model, thermal stress associated with one or more regions of the 3D model, and/or another thermal characteristics associated with one or more regions of the 3D model. The physics behavior can be physics behavior of the thermal characteristics. For instance, the physics behavior can be simulated physics and/or changes of the thermal characteristics. Furthermore, the physics behavior can be simulated thermal conditions associated with the 3D model. The physics behavior can also include correlations and/or behavior determined based on one or more mathematical equations associated with thermal characteristics such as, for example, conservation equations for mass associated with thermal characteristics, conservation equations for momentum associated with thermal characteristics, conservation equations for energy associated with thermal characteristics, conservation equations for angular momentum associated with thermal characteristics, and/or another mathematical equation associated with thermal characteristics.

Additionally or alternatively, the machine learning component 106 can predict combustion characteristics and physics behavior associated with the 3D model. For instance, the machine learning component 106 can perform a machine learning process associated with combustion characteristics associated with the 3D model. The machine learning component 106 can perform the machine learning process based on input data indicative of input received by a device associated with the 3D model. For example, the input data can include the fluid data indicative of a fluid provided to a device associated with the 3D model. Additionally or alternatively, the input data can include electrical data indicative of a voltage and/or a current provided to a device associated with the 3D model. Additionally or alternatively, the input data can include chemical data indicative of a chemical element provided to a device associated with the 3D model. The input data can by employed by the machine learning component 106 to predict the combustion characteristics. The combustion characteristics can be, for example, information related to a chemical reaction associated with one or more regions of the 3D model such as, for example, a temperature measurement, a heating value, an elemental composition, a moisture content, a density, an acoustic measurement and/or another combustion characteristic associated with one or more regions of the 3D model. The physics behavior can be physics behavior of the combustion characteristics. For instance, the physics behavior can be simulated physics and/or changes of the combustion characteristics. Furthermore, the physics behavior can be simulated combustion conditions associated with the 3D model. The physics behavior can also include correlations and/or behavior determined based on one or more mathematical equations associated with combustion characteristics such as, for example, conservation equations for mass associated with combustion characteristics, conservation equations for momentum associated with combustion characteristics, conservation equations for energy associated with combustion characteristics, conservation equations for angular momentum associated with combustion characteristics, and/or another mathematical equation associated with combustion characteristics.

In an embodiment, the modeling component 104 can integrate a first 3D model associated with a first device (e.g., a first mechanical device and/or a first electronic device) and a second 3D model associated with a second device (e.g., a second mechanical device and/or a second electronic device) to generate a 3D model for a device. For example, a 3D model generated by the modeling component 104 can be a combination of two or more 3D models. In an aspect, first geometric features of the first 3D model can be combined with second geometric features of the second 3D model. The first geometric features of the first 3D model can include, for example, chambers, cavities, channels, and/or other geometric features of the first 3D model. Similarly, the second geometric features of the second 3D model can include, for example, chambers, cavities, channels, and/or other geometric features of the second 3D model. As such, chambers, cavities, channels, and/or other geometric features of the first 3D model and the second 3D model can be combined. In another embodiment, the first 3D model can comprise a first set of supply nodes and a first set of sink nodes that form a first flow network for characteristics of the first 3D model. For instance, fluid provided through the first 3D model can flow from a supply node to a sink node of the first 3D model. Additionally, the second 3D model can comprise a second set of supply nodes and a second set of sink nodes that form a second flow network for characteristics of the second 3D model. For instance, fluid provided through the second 3D model can flow from a supply node to a sink node of the second 3D model. The modeling component 104 can combine the first flow network of the first 3D model with the second flow network of the second 3D model. For example, the first set of supply nodes of the first 3D model can be combined with the second set of supply nodes of the second 3D model. Furthermore, the first set of sink nodes of the first 3D model can be combined with the second set of sink nodes of the second 3D model.

In another embodiment, the machine learning component 106 can perform a first machine learning process associated with the first 3D model and a second machine learning process associated with the second 3D model. For instance, the machine learning component 106 can perform learning (e.g., explicit learning and/or implicit learning) and/or can generate inferences with respect to the first 3D model via the first machine learning process. Furthermore, the machine learning component 106 can perform learning (e.g., explicit learning and/or implicit learning) and/or can generate inferences with respect to the second 3D model via the second machine learning process. The learning and/or generated inferences by the machine learning component 106 can facilitate determination of one or more characteristics associated with the one or more 3D models generated by the modeling component 104. Furthermore, the learning and/or generated inferences can be determined by the machine learning component 106 via one or more machine learning processes associated with the one or more 3D models. In an aspect, the machine learning component 106 can predict one or more characteristics of the device based on the one or more first characteristics associated with the first 3D model and the one or more second characteristics associated with the second 3D model. In one example, the machine learning component 106 can predict the one or more characteristics of the device based on the one or more first characteristics and the one or more second characteristics. The one or more first characteristics can include first fluid flow characteristics associated with the first 3D model, first thermal characteristics associated with the first 3D model, first combustion characteristics associated with the first 3D model and/or first physics behavior characteristics associated with the first 3D model. Furthermore, one or more second characteristics can include second fluid flow characteristics associated with the second 3D model, second thermal characteristics associated with the second 3D model, second combustion characteristics associated with the second 3D model and/or second physics behavior characteristics associated with the second 3D model. In an embodiment, the machine learning component 106 can facilitate interaction between the first 3D model and the second 3D model based on the input data associated with the machine learning component 106. For example, interaction of the one or more first characteristics associated with the first 3D model and the one or more second characteristics associated with the second 3D model can be determined by the machine learning component 106 based on the input data.

The 3D design component 108 can provide a 3D design environment associated with the 3D model. For instance, the 3D design component 108 can provide a 3D design environment associated with a mechanical element and/or a 3D model generated by the modeling component 104. The 3D design environment can be a single fluid system design tool. For example, the 3D design environment can be a tool that provides functionality of numerous tools with respect to fluid systems to provide multi-disciplinary type analyses. In one example, the 3D design environment can provide a flow integrated design environment, a heat transfer design environment and/or a combustion design environment. In another example, the 3D design environment can be a combustion design environment solver associated with the 3D design component 108. The 3D design environment associated with the 3D design component 108 can be employed to apply one or more numerical schemes to create predictions for machine simulated conditions. Prediction can be displayed and analyzed on a visual representation of actual hardware using a post-processing module of a graphical user interface. In an aspect, the 3D design environment associated with the 3D design component 108 can generate simulation predictions by conserving governing conservation equations for mass, momentum, energy, angular momentum, and/or species utilizing numerical analysis schemes. In certain embodiments, the fluid model tool component 102 can be employed as a service. For example, the 3D model associated with the fluid model tool component 102 can be a generated computational model employed by the 3D design environment.

In an embodiment, the 3D design environment can render physics modeling data of the device based on the input data and the one or more characteristics of the mechanical device on the 3D model. The physics modeling data can be indicative of a visual representation of the fluid flow, the thermal characteristics, the combustion characteristics and/or the physics behavior with respect to the 3D model. The physics modeling data can also be rendered on the 3D model as one or more dynamic visual elements. In an aspect, the 3D design component 108 can alter visual characteristics (e.g., color, size, hues, shading, etc.) of at least a portion of the physics modeling data based on the fluid flow, the thermal characteristics, the combustion characteristics and/or the physics behavior. For example, different degrees of fluid flow through the 3D model can be presented as different visual characteristics (e.g., colors, sizes, hues or shades, etc.), different degrees of thermal characteristics with respect to the 3D model can be presented as different visual characteristics (e.g., colors, sizes, hues or shades, etc.), different degrees of combustion characteristics with respect to the 3D model can be presented as different visual characteristics (e.g., colors, sizes, hues or shades, etc.), different degrees of physics behavior with respect to the 3D model can be presented as different visual characteristics (e.g., colors, sizes, hues or shades, etc.), etc. In another aspect, the 3D design environment for the 3D model can allow a user to zoom into or out from the 3D model associated with the physics modeling data, rotate a view for the 3D model associated with the physics modeling data, etc. As such, a user can view, analyze and/or interact with the 3D model associated with the physics modeling data to facilitate determination of impact of a fluid flow, thermal characteristics, combustion characteristics and/or physics behavior with respect to a design of the device associated with the 3D model.

The data collection component 109 can collect machine data from a device associated with the 3D model. For example, a device can be constructed based on the 3D model and employed for one or more technological purposes. As such, the device can be a physical representation of the 3D model. In certain embodiments, the data collection component 109 can collect the machine data via a network device of a communication network to update the 3D model and/or physics modeling data associated with the 3D model. In an embodiment, the data collection component 109 can receive the machine data from one or more sensor devices associated with the device. In an aspect the machine learning component 106 can perform a machine learning process based on the machine data to train and/or refine the 3D model. Furthermore, the modeling component 104 can generate a modified version of the 3D model based on the machine learning process associated with the machine data. Additionally or alternatively, the machine learning component 106 can generate a modified version of the physics modeling data for the 3D model based on the machine learning process associated with the machine data. In an aspect, the machine data can be real-time data that is collected by the data collection component approximately in real-time from the device and/or one or more sensor devices associated with the device.

Figure 2:
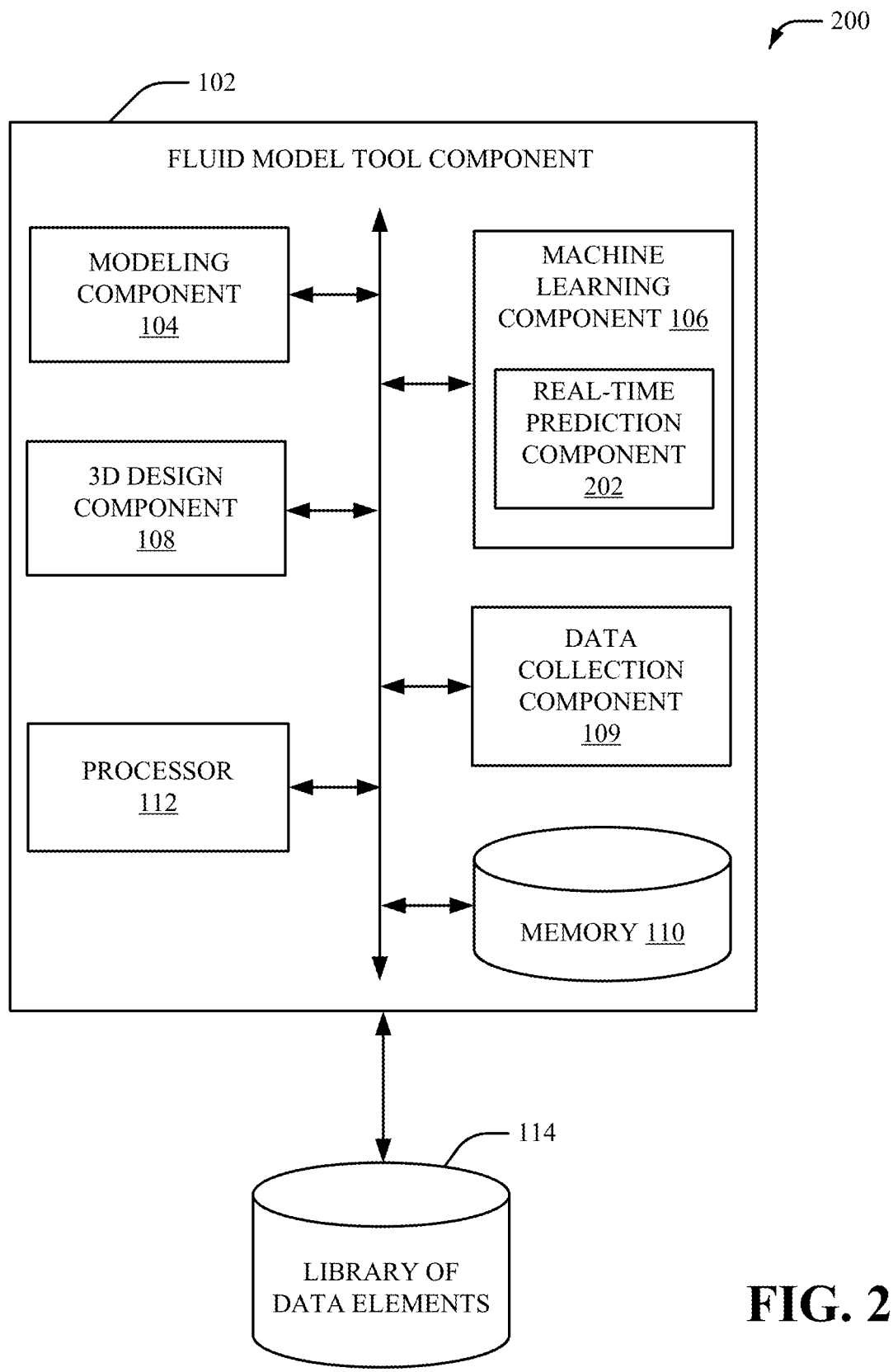
FIG. 2 illustrates a high-level block diagram of another example fluid model tool component, in accordance with various aspects and implementations described herein.

Referring now to FIG. 2, there is illustrated an example system 200 that provides a multiple fluid model tool for interdisciplinary fluid modeling, according to an aspect of the subject disclosure. Repetitive description of like elements employed in other embodiments described herein is omitted for sake of brevity.

The system 200 can include the fluid model tool component 102 and/or the library of data elements 114. The fluid model tool component 102 can include the modeling component 104, the machine learning component 106, the 3D design component 108, the memory 110 and/or the processor 112. In the embodiment shown in FIG. 2, the machine learning component 106 can include a real-time prediction component 202. The real-time prediction component 202 can perform a machine learning process associated with real-time prediction of physics modeling data for the 3D model associated with the 3D design environment. In an aspect, the real-time prediction component 202 can employ machine data collected from the data collection component 109 to perform real-time prediction of physics modeling data for the 3D model associated with the 3D design environment. For example, the real-time prediction component 202 can perform a machine learning process based on the machine data to modify the physics modeling data (e.g., to generate a modified version of physics modeling data for the 3D model associated with the 3D design environment). The real-time prediction component 202 can also facilitate optimization of prototype and/or design of a device associated with the 3D model based on the machine data. In an embodiment, the real-time prediction component 202 can provide real-time fluid flow associated with the 3D model, real-time thermal characteristics associated with the 3D model, real-time combustion characteristics associated with the 3D model and/or real-time physics behavior associated with the 3D model. In one example, the modified version of the physics modeling data provided by the real-time prediction component 202 can simulate real-time physical phenomena associated with the 3D model such as, but not limited to, real-time compressible fluid flow associated with the 3D model, real-time incompressible fluid flow associated with the 3D model, real-time buoyancy driven flow associated with the 3D model, real-time rotating cavity system flow associated with the 3D model, real-time conduction heat transfer associated with the 3D model, real-time convection heat transfer associated with the 3D model, real-time radiation heat transfer associated with the 3D model, real-time combustion equilibrium-chemistry associated with the 3D model, real-time species transport associated with the 3D model, and/or other real-time physics behavior associated with the 3D model.

Figure 3:
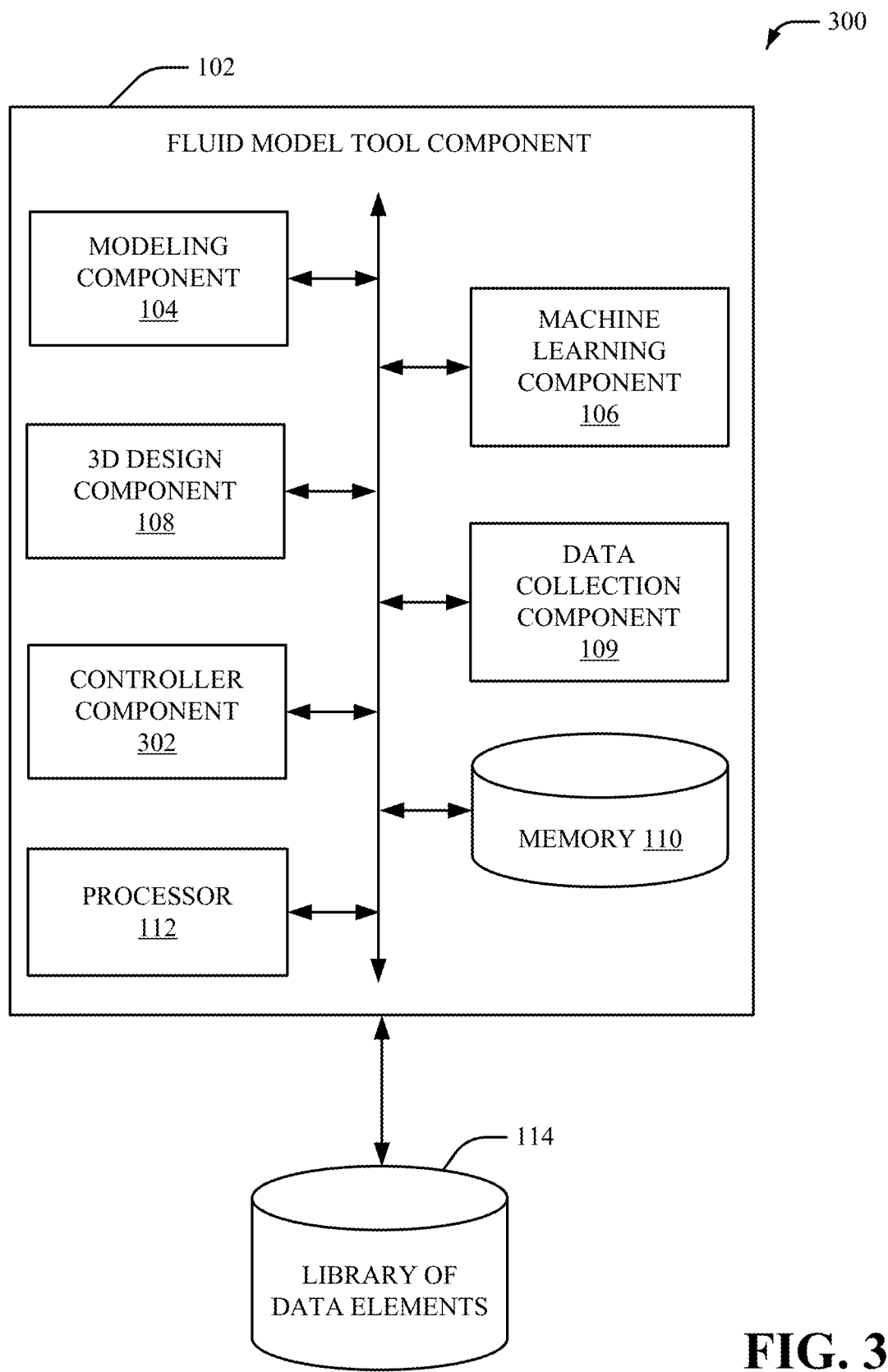
FIG. 3 illustrates a high-level block diagram of yet another example fluid model tool component, in accordance with various aspects and implementations described herein.

Referring now to FIG. 3, there is illustrated an example system 300 that provides a multiple fluid model tool for interdisciplinary fluid modeling, according to an aspect of the subject disclosure. Repetitive description of like elements employed in other embodiments described herein is omitted for sake of brevity.

The system 300 can include the fluid model tool component 102 and/or the library of data elements 114. The fluid model tool component 102 can include the modeling component 104, the machine learning component 106, the 3D design component 108, a controller component 302, the memory 110 and/or the processor 112. In certain embodiments, the machine learning component 106 can include the real-time prediction component 202. The controller component 302 can generate control data to control one or more operations of a device (e.g., a mechanical device and/or an electrical device) associated with the 3D model based on the 3D model and/or the physics modeling data for the 3D model. In an embodiment, the control data can include maintenance data indicative of maintenance information for the device. The controller component 302 can transmit the maintenance data to the device to control one or more operations related to maintenance for the device. In an embodiment, the control data can include diagnostic data indicative of diagnostic information for the device. The controller component 302 can transmit the diagnostic data to the device to control one or more operations related to diagnostics for the device.

Figure 4:
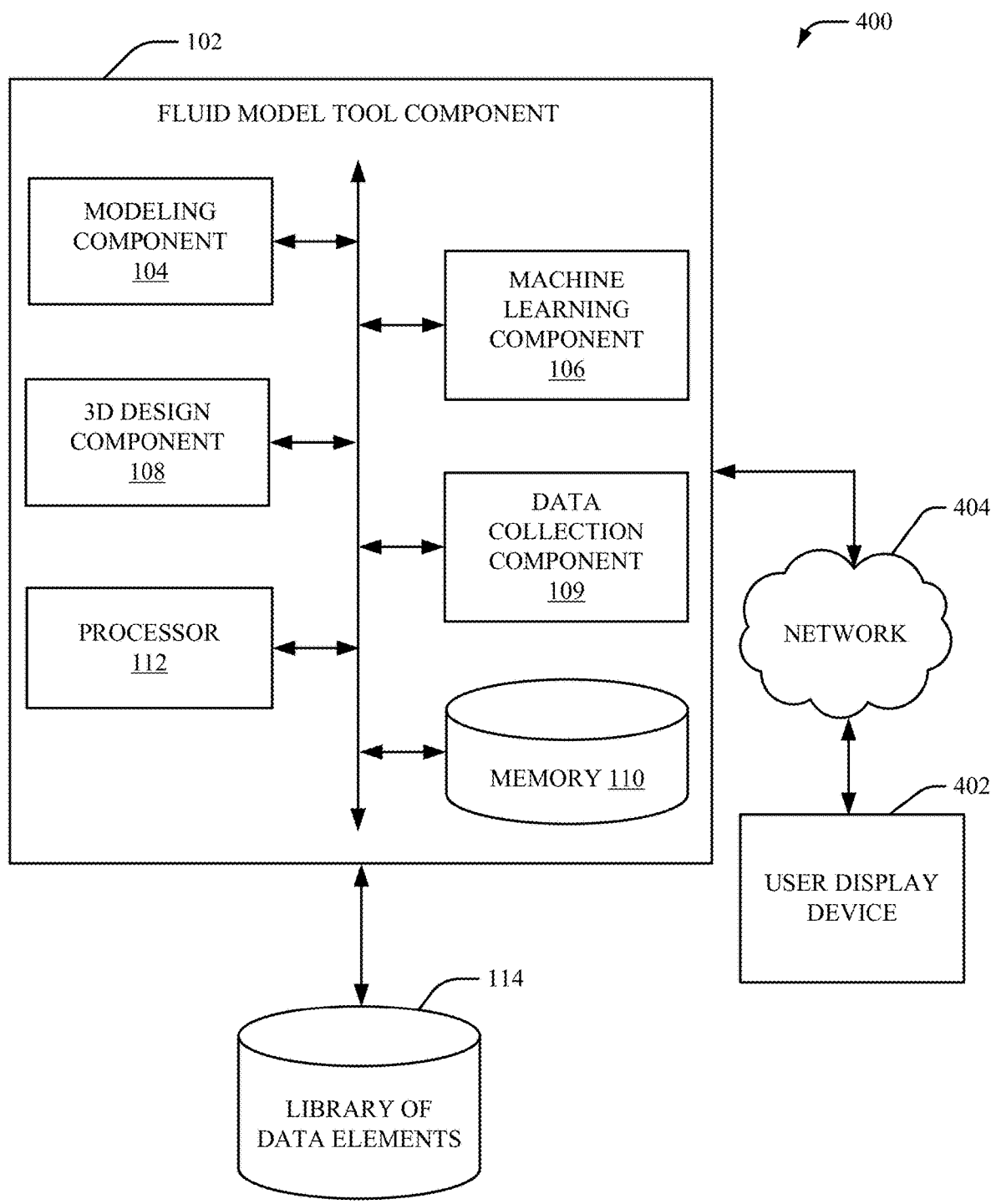
FIG. 4 illustrates a high-level block diagram of an example fluid model tool component in communication with a user display device, in accordance with various aspects and implementations described herein.

Referring now to FIG. 4, there is illustrated an example system 400 that provides a multiple fluid model tool for interdisciplinary fluid modeling, according to an aspect of the subject disclosure. Repetitive description of like elements employed in other embodiments described herein is omitted for sake of brevity.

The system 400 can include the fluid model tool component 102, the library of data elements 114 and a user display device 402. The user display device 402 can be in communication with the fluid model tool component 102 via a network 404. The network 404 can be a wired network and/or a wireless network. The fluid model tool component 102 can include the modeling component 104, the machine learning component 106, the 3D design component 108, the data collection component 109, the controller component 302, the memory 110 and/or the processor 112. In certain embodiments, the machine learning component 106 can include the real-time prediction component 302. The user display device 402 can display a 3D model and/or a 3D design environment generated by the fluid model tool component 102. For example, a 3D model associated with physics modeling data can be rendered on a graphical user interface associated with a display of the user display device 402. The user display device 402 can be a device with a display such as, but not limited to, a computing device, a computer, a desktop computer, a laptop computer, a monitor device, a smart device, a smart phone, a mobile device, a handheld device, a tablet, a portable computing device or another type of user device associated with a display.

Figure 5:
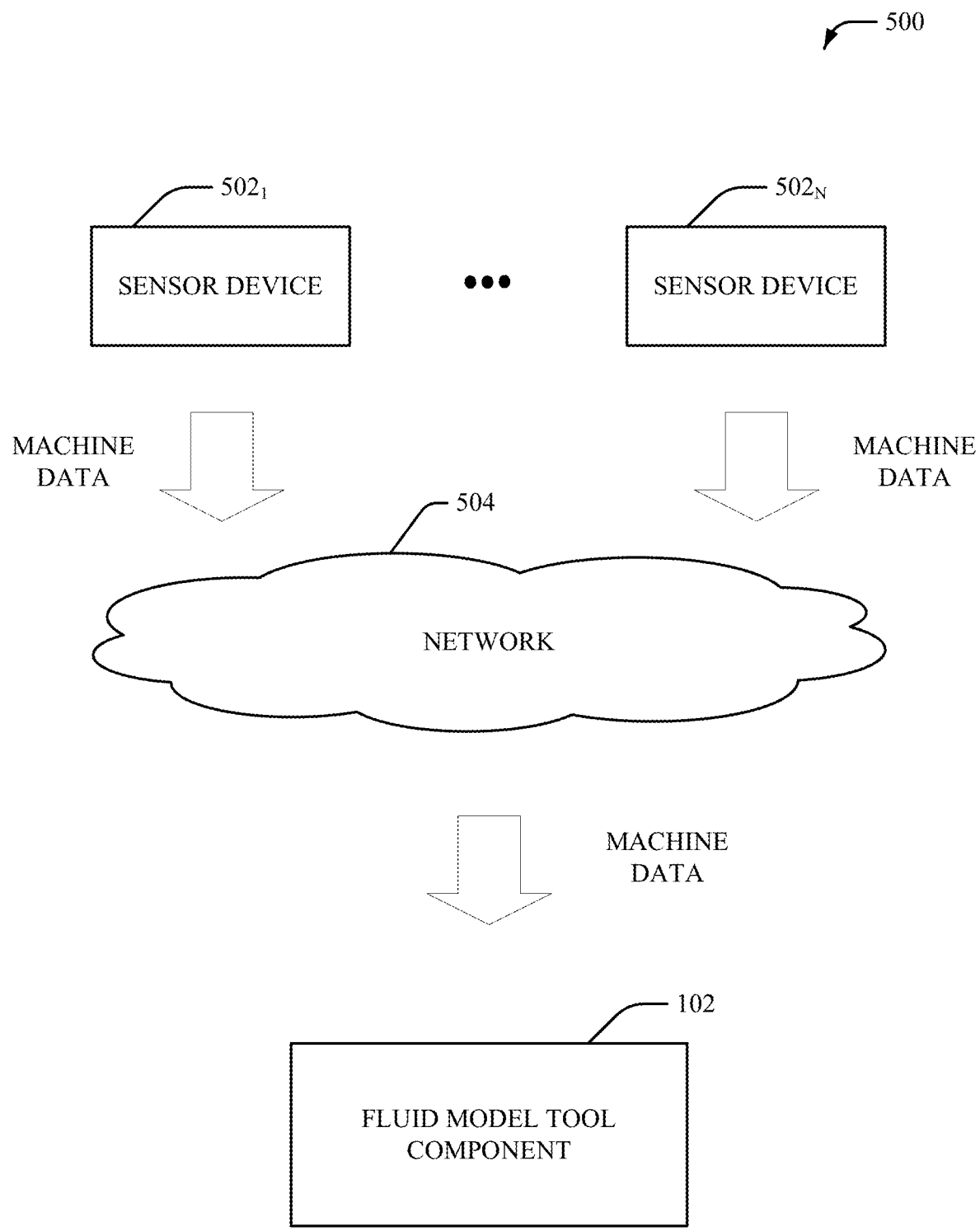
FIG. 5 illustrates an example system that facilitates for training and/or refining of fluid models using disparate and/or aggregated machine data, in accordance with various aspects and implementations described herein.

Referring now to FIG. 5, there is illustrated an example system 500 that provides interdisciplinary fluid modeling, according to an aspect of the subject disclosure. Repetitive description of like elements employed in other embodiments described herein is omitted for sake of brevity.

The system 500 can include the fluid model tool component 102 and one or more sensor devices $502_{1-N}$, where N is an integer. The one or more sensor devices $502_{1-N}$ can generate machine data (e.g., MACHINE DATA shown in FIG. 5). The machine data can be transmitted to the fluid model tool component 102 via a network 504. For instance, the data collection component 109 of the fluid model tool component 102 can collect, via the network 504, the machine data generated by the one or more sensor devices $502_{1-N}$. The modeling component 104 and/or the machine learning component 106 can employ the machine data generated by the one or more sensor devices $502_{1-N}$ to update the 3D model associated with the 3D design environment. The network 504 can be a wired network and/or a wireless network. Furthermore, the network 504 can include one or more network devices to facilitate transmission of the machine data to the fluid model tool component 102. In an embodiment, the fluid model tool component 102 can be implemented on a cloud platform. In an embodiment, the fluid model tool component 102 (e.g., a graphical user interface provided by the fluid model tool component 102) can provide a live data feed associated with the machine data generated by the one or more sensor devices $502_{1-N}$. The live data feed can be associated with a digital display of a status of the one or more sensor devices $502_{1-N}$. As such, an issue associated with the one or more sensor devices $502_{1-N}$ can be identified with greater precision and/or efficiency.

Figure 6:
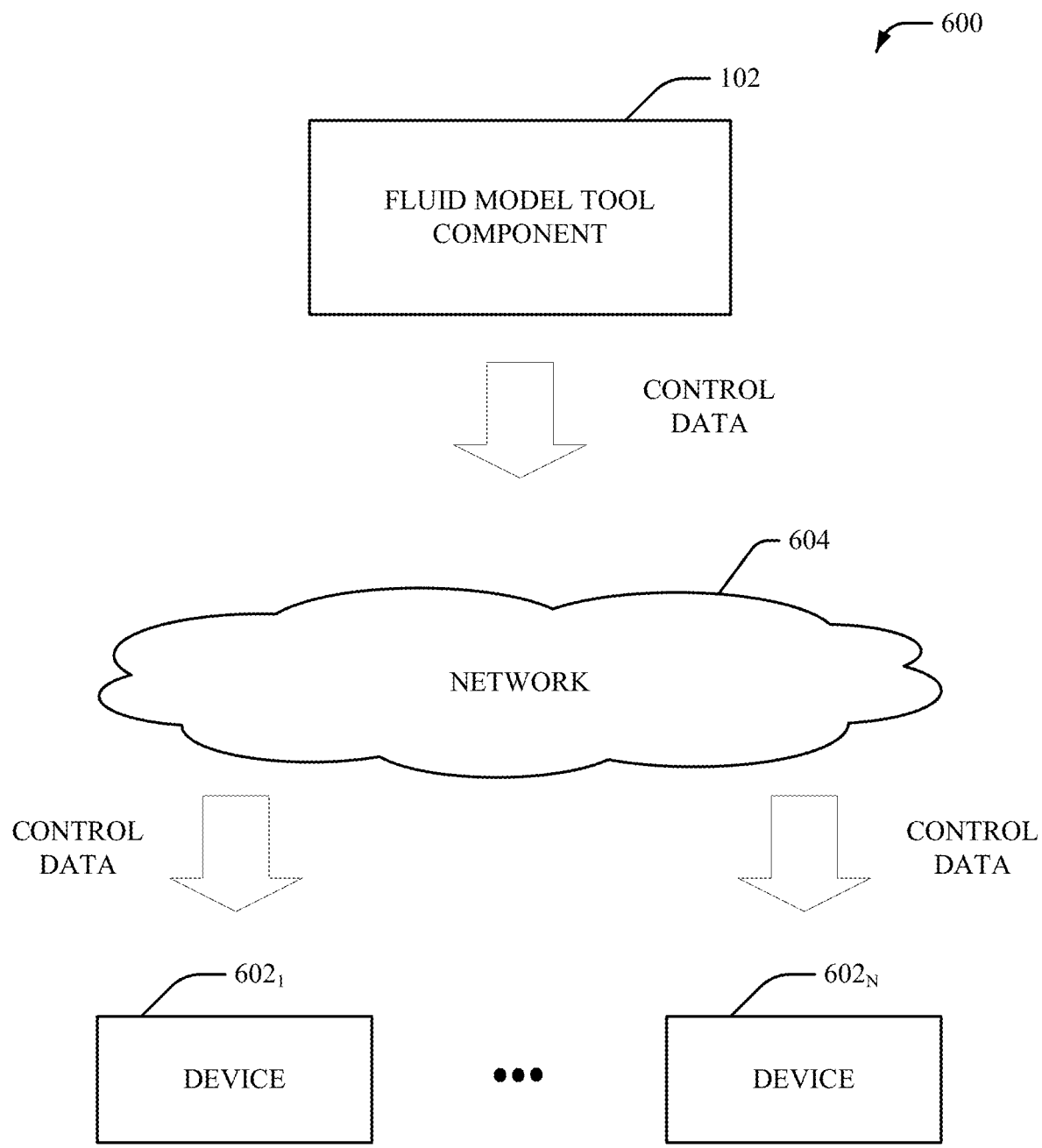
FIG. 6 illustrates another example system that facilitates for training and/or refining of fluid models using disparate and/or aggregated machine data, in accordance with various aspects and implementations described herein.

Referring now to FIG. 6, there is illustrated an example system 600 that provides interdisciplinary fluid modeling, according to an aspect of the subject disclosure. Repetitive description of like elements employed in other embodiments described herein is omitted for sake of brevity.

The system 600 can include the fluid model tool component 102 and one or more devices $602_{1-N}$, where N is an integer. In one example, the one or more devices $602_{1-N}$ can include one or more machines and/or one or more machine systems. The fluid model tool component 102 can generate control data (e.g., CONTROL DATA shown in FIG. 6). The control data can be transmitted to the one or more devices $602_{1-N}$ via a network 604. For instance, the controller component 302 of the fluid model tool component 102 can transmit, via the network 604, the control data to the one or more devices $602_{1-N}$. The network 604 can be a wired network and/or a wireless network. Furthermore, the network 604 can include one or more network devices to facilitate transmission of the control data to the one or more devices $602_{1-N}$. In an embodiment, the fluid model tool component 102 can be implemented on a cloud platform. The controller component 302 of the fluid model tool component 102 can transmit the control data to the one or more devices $602_{1-N}$ to control one or more operations of the one or more devices $602_{1-N}$. In an embodiment, the control data can include maintenance data indicative of maintenance information for the one or more devices $602_{1-N}$. The controller component 302 of the fluid model tool component 102 can transmit, via the network 604, the maintenance data to the one or more devices $602_{1-N}$ to control one or more operations related to maintenance for the one or more devices $602_{1-N}$. In an embodiment, the control data can include diagnostic data indicative of diagnostic information for the device. The controller component 302 of the fluid model tool component 102 can transmit, via the network 604, the diagnostic data to the one or more devices $602_{1-N}$ to control one or more operations related to diagnostics for the one or more devices $602_{1-N}$. In an aspect, one or more 3D models generated by the fluid model tool component 102 can model and/or provide physics modeling data for the one or more devices $602_{1-N}$.

Figure 7:
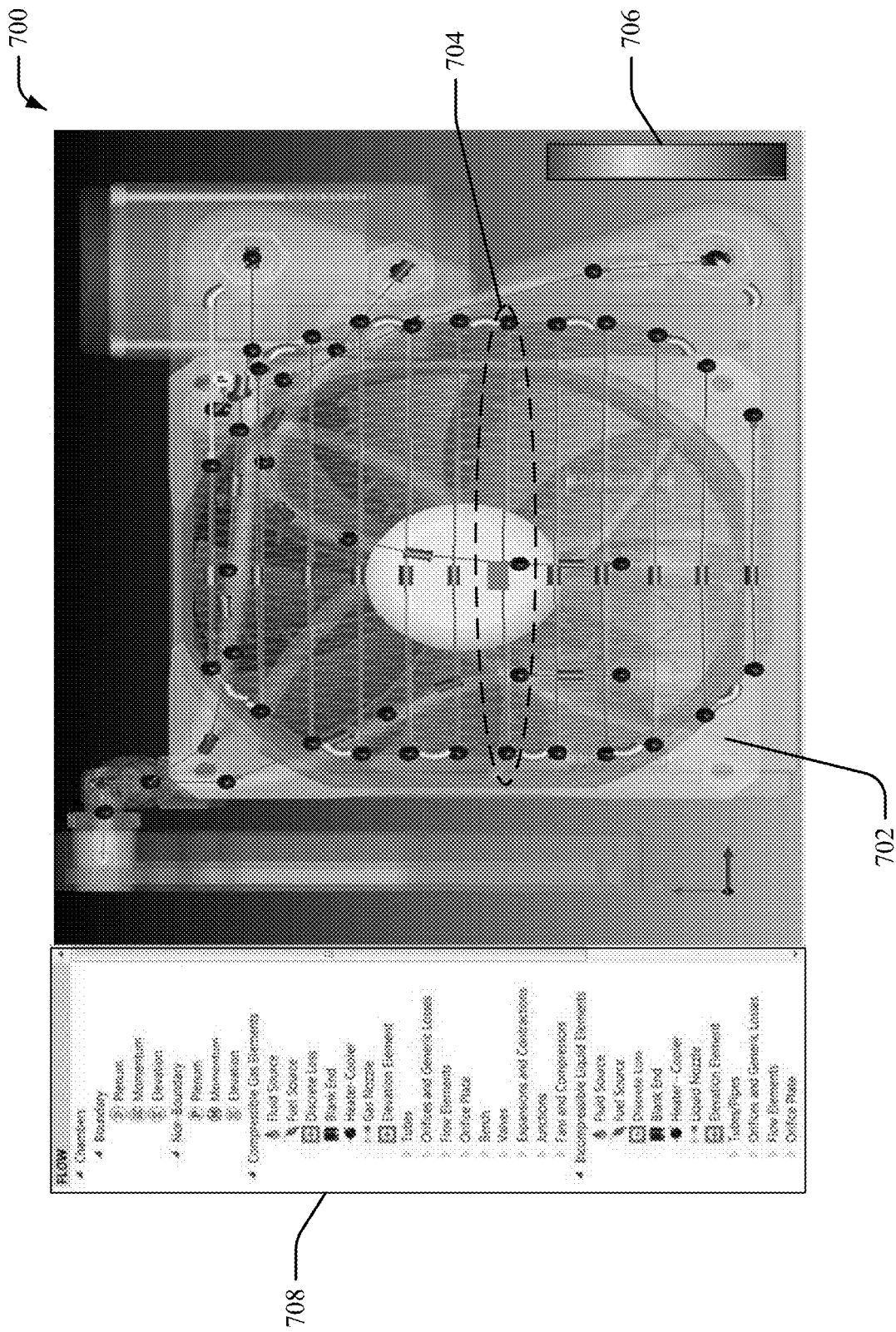
FIG. 7 illustrates an example 3D model, in accordance with various aspects and implementations described herein.

FIG. 7 illustrates an example 3D model 700, in accordance with various aspects and implementations described herein. The 3D model 700 can, for example, correspond to a 3D model generated by the fluid model tool component 102. The 3D model 700 can illustrate fluid dynamics, thermal dynamic and/or combustion dynamics with respect to a design of a device. For example, the 3D model 700 can be a 3D model where physics modeling data associated with fluid dynamics, thermal dynamic and/or combustion dynamics is rendered on a device. In an aspect, the 3D model 700 can include a device portion 702 of the 3D model 700 and physics modeling data 704 that is rendered on the device portion 702. Visual characteristics (e.g., a color, a size, a hues, shading, etc.) of the physics modeling data 704 can be dynamic based on a value of the physics modeling data 704.

For instance, a first portion of the physics modeling data 704 associated with first physics modeling information can comprise a first visual characteristics and a second portion of the physics modeling data 704 associated with second physics modeling information can comprise a second visual characteristic. In an embodiment, the physics modeling data 704 can be determined by the machine learning component 106. In one example, the physics modeling data 704 can be associated with a set of control volumes and/or a flow network related to fluid dynamics, thermal dynamic and/or combustion dynamics. In an embodiment, a 3D design environment associated with the 3D model 700 can include a heat bar 706. The heat bar 706 can include a set of colors that correspond to different values for the physics modeling data 704. For example, a first color (e.g., a color red) in the heat bar 706 can correspond to a first value for the physics modeling data 704 and a second color (e.g., a color blue) in the heat bar 706 can correspond to a second value for the physics modeling data 704. In another embodiment, a 3D design environment associated with the 3D model 700 can include a side bar 708. The side bar 708 can include information to facilitate generation of the 3D model 700 and/or the physics modeling data 704. For example, the side bar 708 can facilitate selection of one or more sub-components (e.g., flow elements, tubes, orifices, bends valves, junctions, fans, compressors, another other component, etc.) that form the device portion 702 of the 3D model 700. In another example, the side bar 708 can facilitate selection of a type of physics modeling data (e.g., flow dynamics, thermal dynamics, combustion dynamics, etc.) provided by the physics modeling data 704.

Figure 8:
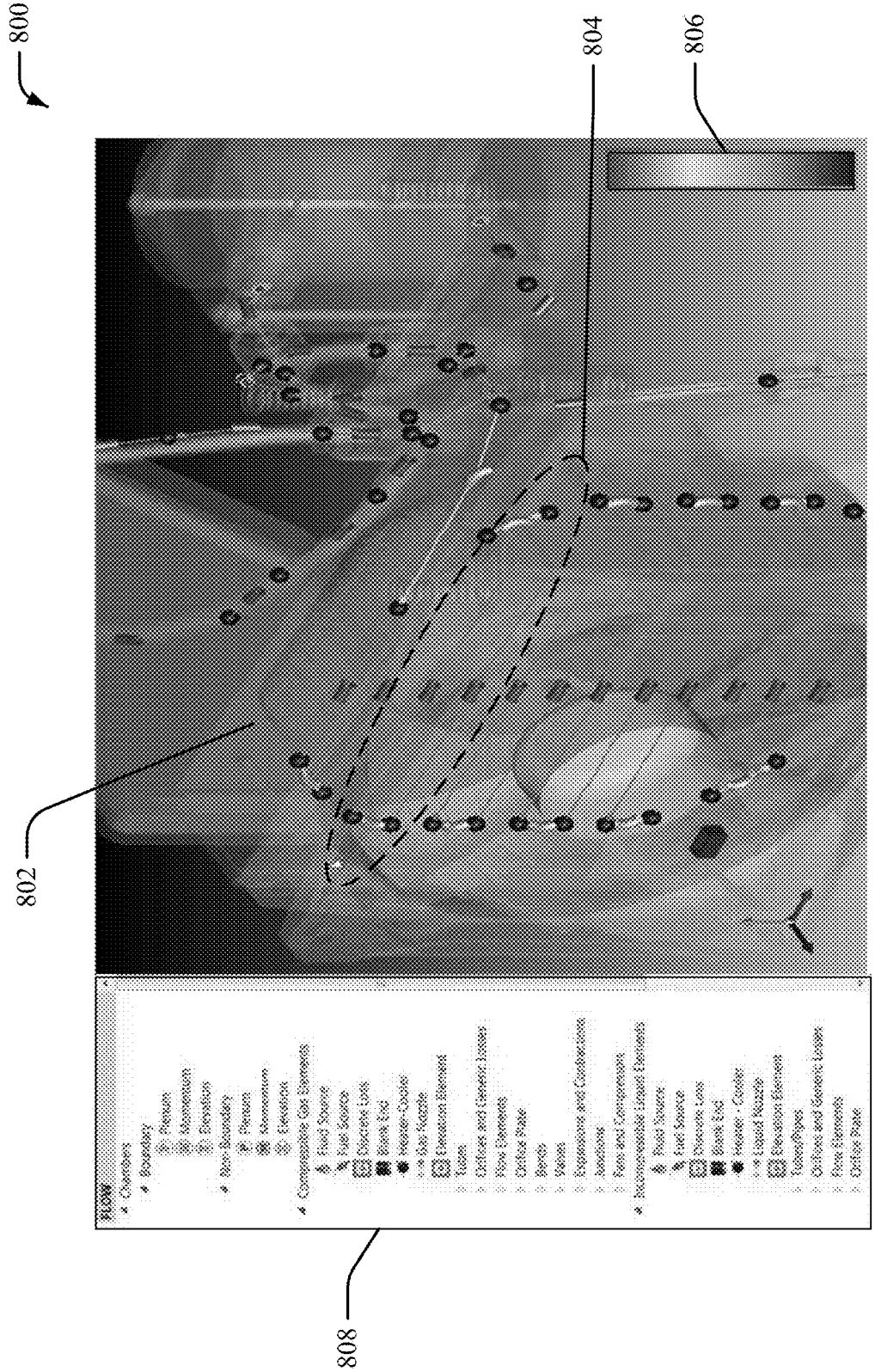
FIG. 8 illustrates another example 3D model, in accordance with various aspects and implementations described herein.

FIG. 8 illustrates an example 3D model 800, in accordance with various aspects and implementations described herein. The 3D model 800 can, for example, correspond to a 3D model generated by the fluid model tool component 102. The 3D model 800 can illustrate fluid dynamics, thermal dynamic and/or combustion dynamics with respect to a design of a device. For example, the 3D model 800 can be a 3D model where physics modeling data associated with fluid dynamics, thermal dynamic and/or combustion dynamics is rendered on a device. In an aspect, the 3D model 800 can include a device portion 802 of the 3D model 800 and physics modeling data 804 that is rendered on the device portion 802. Visual characteristics (e.g., a color, a size, a hues, shading, etc.) of the physics modeling data 804 can be dynamic based on a value of the physics modeling data 804. For instance, a first portion of the physics modeling data 804 associated with first physics modeling information can comprise a first visual characteristics and a second portion of the physics modeling data 804 associated with second physics modeling information can comprise a second visual characteristic. In an embodiment, the physics modeling data 804 can be determined by the machine learning component 106. In one example, the physics modeling data 804 can be associated with a set of control volumes and/or a flow network related to fluid dynamics, thermal dynamic and/or combustion dynamics. In an embodiment, a 3D design environment associated with the 3D model 800 can include a heat bar 806. The heat bar 806 can include a set of colors that correspond to different values for the physics modeling data 804. For example, a first color (e.g., a color red) in the heat bar 806 can correspond to a first value for the physics modeling data 804 and a second color (e.g., a color blue) in the heat bar 806 can correspond to a second value for the physics modeling data 804. In another embodiment, a 3D design environment associated with the 3D model 800 can include a side bar 808. The side bar 808 can include information to facilitate generation of the 3D model 800 and/or the physics modeling data 804. For example, the side bar 808 can facilitate selection of one or more sub-components (e.g., flow elements, tubes, orifices, bends valves, junctions, fans, compressors, another other component, etc.) that form the device portion 802 of the 3D model 800. In another example, the side bar 808 can facilitate selection of a type of physics modeling data (e.g., flow dynamics, thermal dynamics, combustion dynamics, etc.) provided by the physics modeling data 804.

Figure 9:
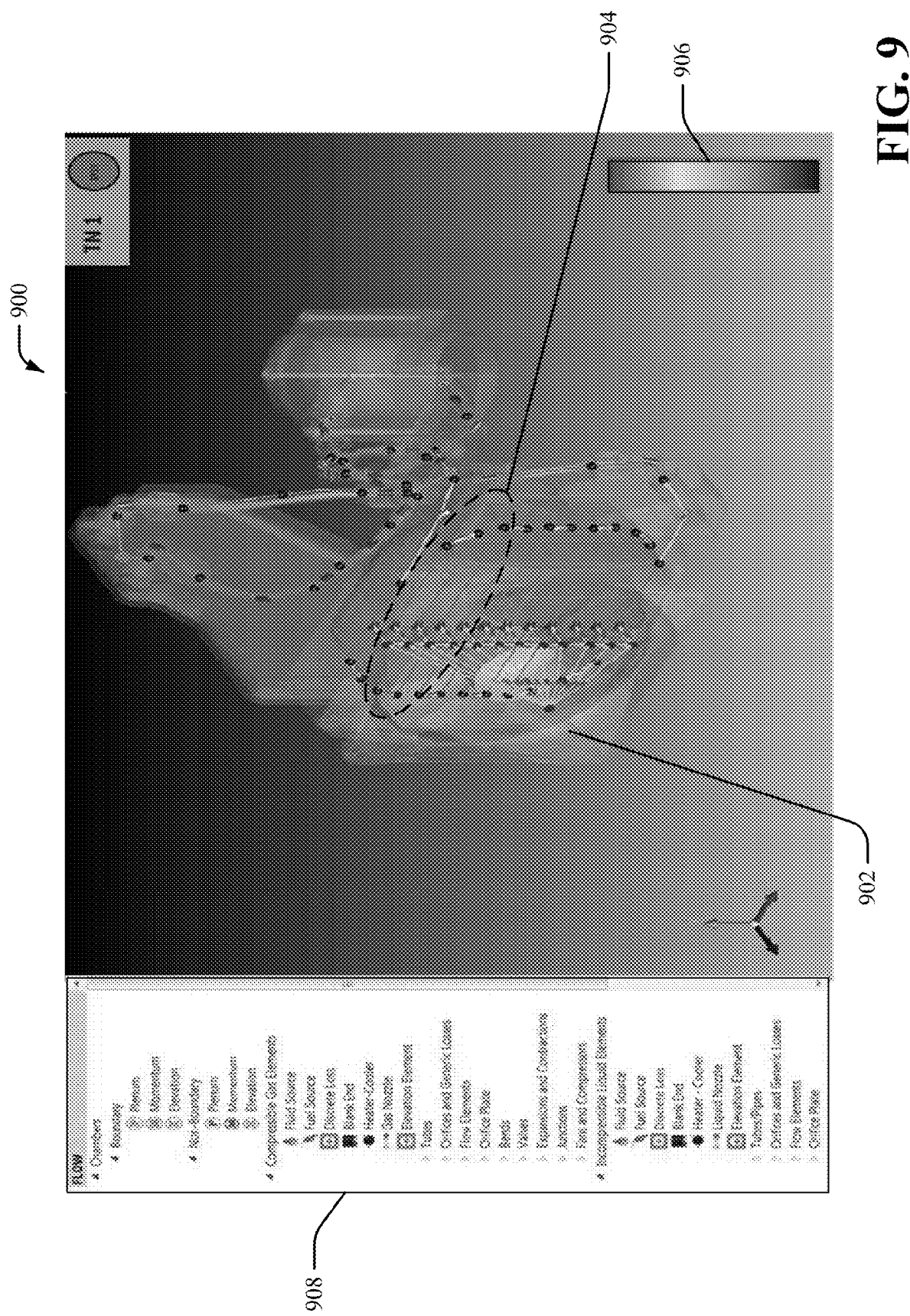
FIG. 9 illustrates yet another example 3D model, in accordance with various aspects and implementations described herein.

FIG. 9 illustrates an example 3D model 900, in accordance with various aspects and implementations described herein. The 3D model 900 can, for example, correspond to a 3D model generated by the fluid model tool component 102. The 3D model 900 can illustrate fluid dynamics, thermal dynamic and/or combustion dynamics with respect to a design of a device. For example, the 3D model 900 can be a 3D model where physics modeling data associated with fluid dynamics, thermal dynamic and/or combustion dynamics is rendered on a device. In an aspect, the 3D model 900 can include a device portion 902 of the 3D model 900 and physics modeling data 904 that is rendered on the device portion 902. Visual characteristics (e.g., a color, a size, a hues, shading, etc.) of the physics modeling data 904 can be dynamic based on a value of the physics modeling data 904. For instance, a first portion of the physics modeling data 904 associated with first physics modeling information can comprise a first visual characteristics and a second portion of the physics modeling data 904 associated with second physics modeling information can comprise a second visual characteristic. In an embodiment, the physics modeling data 904 can be determined by the machine learning component 106. In one example, the physics modeling data 904 can be associated with a set of control volumes and/or a flow network related to fluid dynamics, thermal dynamic and/or combustion dynamics. In an embodiment, a 3D design environment associated with the 3D model 900 can include a heat bar 906. The heat bar 906 can include a set of colors that correspond to different values for the physics modeling data 904. For example, a first color (e.g., a color red) in the heat bar 906 can correspond to a first value for the physics modeling data 904 and a second color (e.g., a color blue) in the heat bar 906 can correspond to a second value for the physics modeling data 904. In another embodiment, a 3D design environment associated with the 3D model 900 can include a side bar 908. The side bar 908 can include information to facilitate generation of the 3D model 900 and/or the physics modeling data 904. For example, the side bar 908 can facilitate selection of one or more sub-components (e.g., flow elements, tubes, orifices, bends valves, junctions, fans, compressors, another other component, etc.) that form the device portion 902 of the 3D model 900. In another example, the side bar 908 can facilitate selection of a type of physics modeling data (e.g., flow dynamics, thermal dynamics, combustion dynamics, etc.) provided by the physics modeling data 904.

Figure 10:
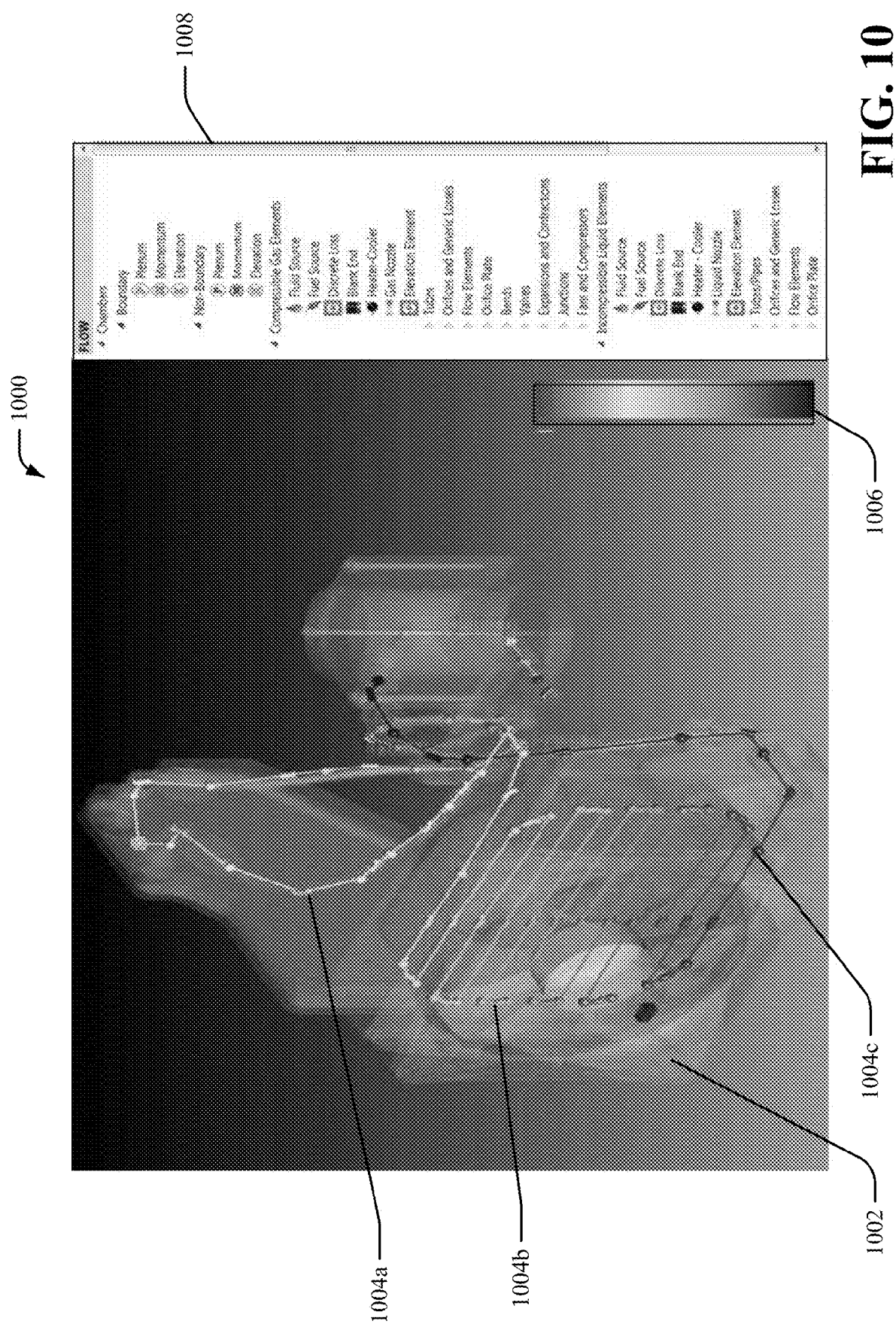
FIG. 10 illustrates yet another example 3D model, in accordance with various aspects and implementations described herein.

FIG. 10 illustrates an example 3D model 1000, in accordance with various aspects and implementations described herein. The 3D model 1000 can, for example, correspond to a 3D model generated by the fluid model tool component 102. The 3D model 1000 can illustrate fluid dynamics, thermal dynamic and/or combustion dynamics with respect to a design of a device. For example, the 3D model 1000 can be a 3D model where physics modeling data associated with fluid dynamics, thermal dynamic and/or combustion dynamics is rendered on a device. In an aspect, the 3D model 1000 can include a device portion 1002 of the 3D model 900. The 3D model 1000 can also include first physics modeling data 1004a, second physics modeling data 1004b and third physics modeling data 1004c that are rendered on the device portion 1002. Visual characteristics (e.g., a color, a size, a hues, shading, etc.) of the first physics modeling data 1004a, the second physics modeling data 1004b and the third physics modeling data 1004c can be dynamic based on a value of the physics modeling data 1004. For instance, the first physics modeling data 1004a can comprise a first visual characteristic (e.g., a yellow color) associated with a first physics modeling data value, the second physics modeling data 1004b can comprise a second visual characteristic (e.g., a green color) associated with a second physics modeling data value, and the third physics modeling data 1004c can comprise a third visual characteristic (e.g., a blue color) associated with a third physics modeling data value. In an embodiment, the first physics modeling data 1004a, the second physics modeling data 1004b and the third physics modeling data 1004c can be determined by the machine learning component 106. In one example, the first physics modeling data 1004a, the second physics modeling data 1004b and the third physics modeling data 1004c can be associated with a set of control volumes and/or a flow network related to fluid dynamics, thermal dynamic and/or combustion dynamics. In an embodiment, a 3D design environment associated with the 3D model 1000 can include a heat bar 1006. The heat bar 1006 can include a set of colors that correspond to different values for the first physics modeling data 1004a, the second physics modeling data 1004b and the third physics modeling data 1004c. For example, a first color (e.g., a color yellow) in the heat bar 1006 can correspond to the first physics modeling data value associated with the first visual characteristic for the first physics modeling data 1004a, a second color (e.g., a color green) in the heat bar 1006 can correspond to the second physics modeling data value associated with the second visual characteristic for the second physics modeling data 1004b, and a third color (e.g., a color blue) in the heat bar 1006 can correspond to the third physics modeling data value associated with the third visual characteristic for the third physics modeling data 1004c. In another embodiment, a 3D design environment associated with the 3D model 1000 can include a side bar 1008. The side bar 1008 can include information to facilitate generation of the 3D model 1000, the first physics modeling data 1004a, the second physics modeling data 1004b and/or the third physics modeling data 1004c. For example, the side bar 1008 can facilitate selection of one or more sub-components (e.g., flow elements, tubes, orifices, bends valves, junctions, fans, compressors, another other component, etc.) that form the device portion 1002 of the 3D model 1000. In another example, the side bar 1008 can facilitate selection of a type of physics modeling data (e.g., flow dynamics, thermal dynamics, combustion dynamics, etc.) provided by the first physics modeling data 1004a, the second physics modeling data 1004b and the third physics modeling data 1004c.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 11:
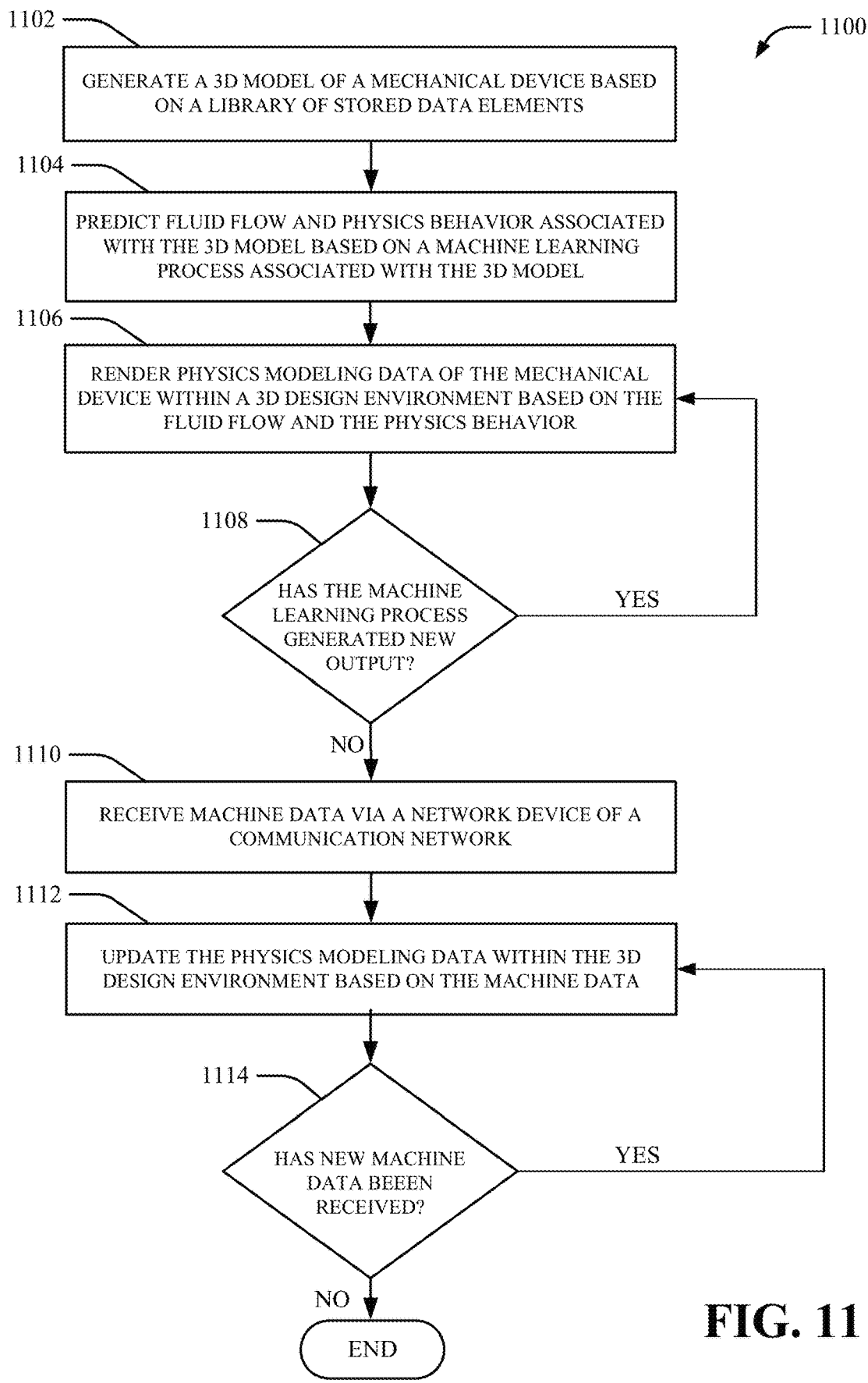
FIG. 11 depicts a flow diagram of an example method for providing interdisciplinary fluid modeling, in accordance with various aspects and implementations described herein.
Figure 12:
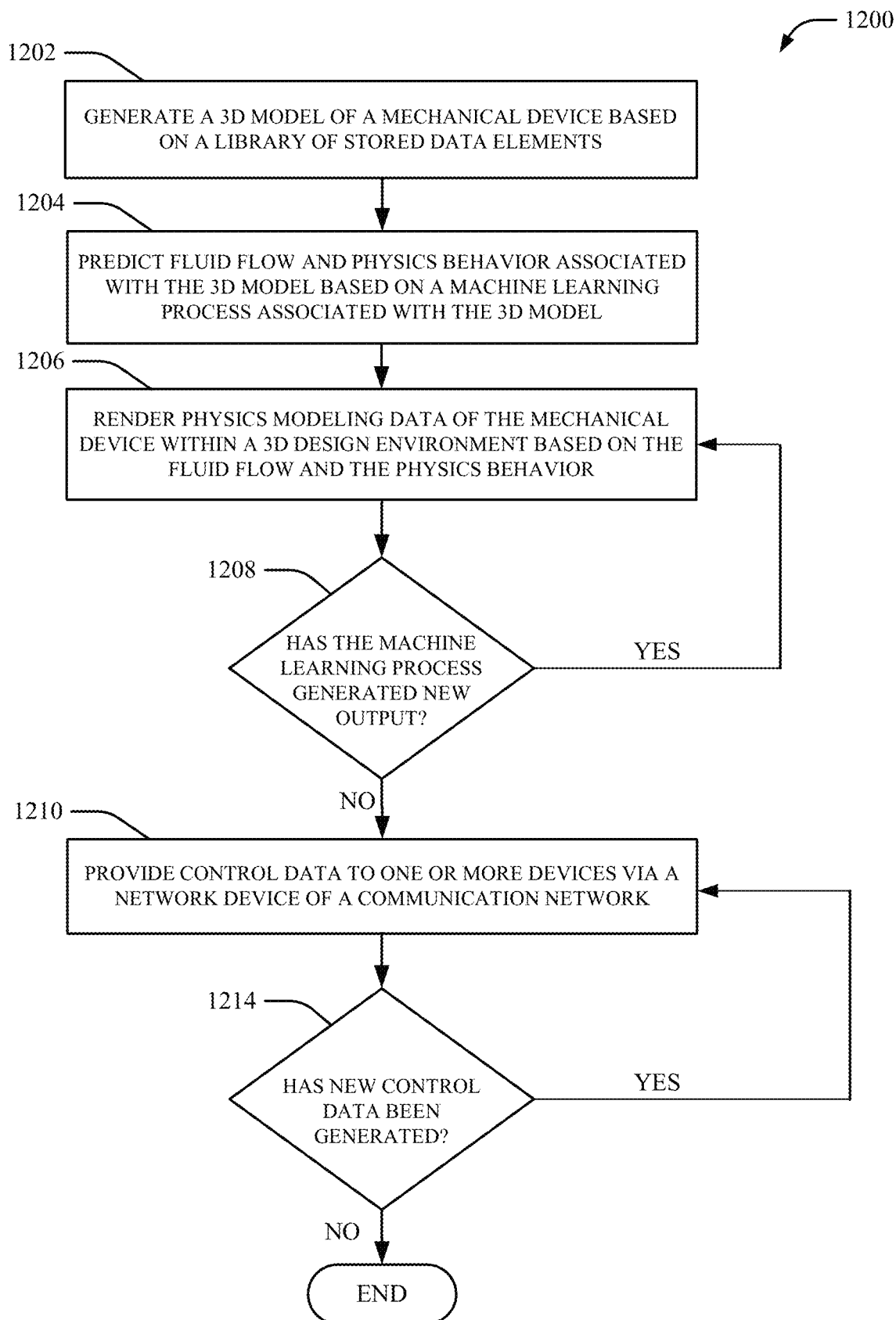
FIG. 12 depicts a flow diagram of another example method for providing interdisciplinary fluid modeling, in accordance with various aspects and implementations described herein.

FIGS. 11-12 illustrate methodologies and/or flow diagrams in accordance with the disclosed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Referring to FIG. 11, there illustrated is a methodology 1100 for providing interdisciplinary fluid modeling, according to an aspect of the subject innovation. As an example, the methodology 1100 can be utilized in various applications, such as, but not limited to, modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, diagnostics systems, prognostics systems, machine design systems, medical device systems, medical imaging systems, medical modeling systems, simulation systems, enterprise systems, enterprise imaging solution systems, advanced diagnostic tool systems, image management platform systems, artificial intelligence systems, machine learning systems, neural network systems, etc. At 1102, a 3D model of a mechanical device is generated (e.g., by modeling component 104) based on a library of stored data elements. The library of data elements 114 can include a set of data elements for mechanical components of the mechanical device and/or electrical components of the mechanical device. The set of data elements can include, for example, geometry data and/or texture data to facilitate generation of the 3D model. In an embodiment, the generating the 3D model can include integrating a first 3D model associated with a first mechanical device and a second 3D model associated with a second mechanical device.

At 1104, fluid flow and physics behavior associated with the 3D model is predicted (e.g., by machine learning component 106) based on a machine learning process associated with the 3D model. The fluid flow can be indicative of behavior related to fluid dynamics associated with the 3D model. The physics behavior can include, for example, thermal characteristics, combustion characteristics and/or physics behavior associated with the 3D model. For instance, the machine learning process can perform learning and/or can generate inferences with respect to fluid flow, thermal characteristics, combustion characteristics and/or physics behavior associated with the 3D model. In an aspect, the machine learning process can also be performed based on input data. The input data can include fluid data, electrical data and/or chemical data associated with an input provided to a device associated with the 3D model. The fluid flow and the physics behavior can also be indicative of behavior related to fluid dynamics, thermal dynamics and/or combustion dynamics throughout the device associated with the 3D model in response to the input data.

At 1106, physics modeling data of the mechanical device is rendered within a 3D design environment (e.g., by 3D design component 108) based on the fluid flow and the physics behavior. For example, the physics modeling data can be generated based on the fluid flow and the physics behavior determined from the machine learning process. The physics modeling data can be indicative of a visual representation of the fluid flow, the thermal characteristics, the combustion characteristics and/or the physics behavior with respect to the 3D model. The 3D design environment can be presented via a graphical user interface that presents the 3D model via a display device and renders the physics modeling data on the 3D model. In an aspect, the physics modeling data can be rendered on the 3D model as dynamic visual elements. In an embodiment, generation of the graphical user interface can include providing the 3D design environment associated with the 3D model.

At 1108, it is determined (e.g., by machine learning component 106) whether the machine learning process has generated new output. If yes, the methodology 1100 returns to 1106 to update the physics modeling data based on the new output. If no, the methodology 1100 proceeds to 1110.

At 1110, machine data is received (e.g., by data collection component 109) via a network device of a communication network. For instance, the machine data can be collected from one or more devices and/or one or more machines located remotely. At least a portion of the one or more devices and/or one or more machines can correspond to a physical representation of the 3D model. For example, a portion of the one or more devices and/or one or more machines can be constructed based on the 3D model and employed for one or more technological purposes. In an aspect, the machine data can be real-time data that is collected via the network device of the communication network approximately in real-time from the one or more devices and/or one or more machines. In an embodiment, the one or more devices and/or one or more machines can include one or more sensor devices that generate the machine data.

At 1112, the physics modeling data within the 3D design environment is updated (e.g., by machine learning component 106) based on the machine data. For example, a visual representation of the fluid flow, the thermal characteristics, the combustion characteristics and/or the physics behavior with respect to the 3D model can be updated based on the machine data. In an aspect, the physics modeling data within the 3D design environment can be updated to provide a visual representation of real-time fluid flow, real-time thermal characteristics, real-time combustion characteristics and/or real-time physics behavior associated with the one or more devices and/or one or more machines.

At 1114, it is determined (e.g., by data collection component 109) whether new machine data has been received. For example, it can be determined whether new machine data is received by the one or more devices and/or the one or more machines. If yes, the methodology 1100 returns to 1112 to update the physics modeling data based on the new machine data. If no, the methodology 1100 can end.

In an embodiment, the methodology 1100 can include performing another machine learning process based on the machine data to generate updated physics modeling data. In another embodiment, the methodology 1100 can include receiving the machine data from one or more sensor devices in communication with the system via the network device. In yet another embodiment, the methodology 1100 can include receiving real-time data approximately in real-time from one or more sensor devices in communication with the system via the network device. In certain embodiments, the methodology 1100 can include rendering the updated physics modeling data within the three-dimensional design environment. In certain embodiments, the methodology 1100 can include generating control data to control one or more operations of a device based on the physics modeling data. Additionally the methodology 1100 can include transmitting the control data to the device.

Referring to FIG. 12, there illustrated is a methodology 1200 for providing interdisciplinary fluid modeling, according to an aspect of the subject innovation. As an example, the methodology 1200 can be utilized in various applications, such as, but not limited to, modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, diagnostics systems, prognostics systems, machine design systems, medical device systems, medical imaging systems, medical modeling systems, simulation systems, enterprise systems, enterprise imaging solution systems, advanced diagnostic tool systems, image management platform systems, artificial intelligence systems, machine learning systems, neural network systems, etc. At 1202, a 3D model of a mechanical device is generated (e.g., by modeling component 104) based on a library of stored data elements. The library of data elements 114 can include a set of data elements for mechanical components of the mechanical device and/or electrical components of the mechanical device. The set of data elements can include, for example, geometry data and/or texture data to facilitate generation of the 3D model. In an embodiment, the generating the 3D model can include integrating a first 3D model associated with a first mechanical device and a second 3D model associated with a second mechanical device.

At 1204, fluid flow and physics behavior associated with the 3D model is predicted (e.g., by machine learning component 106) based on a machine learning process associated with the 3D model. The fluid flow can be indicative of behavior related to fluid dynamics associated with the 3D model. The physics behavior can include, for example, thermal characteristics, combustion characteristics and/or physics behavior associated with the 3D model. For instance, the machine learning process can perform learning and/or can generate inferences with respect to fluid flow, thermal characteristics, combustion characteristics and/or physics behavior associated with the 3D model. In an aspect, the machine learning process can also be performed based on input data. The input data can include fluid data, electrical data and/or chemical data associated with an input provided to a device associated with the 3D model. The fluid flow and the physics behavior can also be indicative of behavior related to fluid dynamics, thermal dynamics and/or combustion dynamics throughout the device associated with the 3D model in response to the input data.

At 1206, physics modeling data of the mechanical device is rendered within a 3D design environment (e.g., by 3D design component 108) based on the fluid flow and the physics behavior. For example, the physics modeling data can be generated based on the fluid flow and the physics behavior determined from the machine learning process. The physics modeling data can be indicative of a visual representation of the fluid flow, the thermal characteristics, the combustion characteristics and/or the physics behavior with respect to the 3D model. The 3D design environment can be presented via a graphical user interface that presents the 3D model via a display device and renders the physics modeling data on the 3D model. In an aspect, the physics modeling data can be rendered on the 3D model as dynamic visual elements. In an embodiment, generation of the graphical user interface can include providing the 3D design environment associated with the 3D model.

At 1208, it is determined (e.g., by machine learning component 106) whether the machine learning process has generated new output. If yes, the methodology 1200 returns to 1206 to update the physics modeling data based on the new output. If no, the methodology 1200 proceeds to 1210.

At 1210, control data is provided (e.g., by controller component 302) to one or more devices via a network device of a communication network. For instance, the control data can be provided to the one or more devices to control one or more operations associated with the one or more devices. In one example, the control data can include maintenance data indicative of information to control one or more operations related to maintenance of the one or more devices. In another example, the control data can include diagnostic data indicative of information to control one or more operations related to diagnostics for the one or more devices. The one or more devices can be located remotely, for example. At least a portion of the one or more devices can correspond to a physical representation of the 3D model. For example, a portion of the one or more devices can be constructed based on the 3D model and employed for one or more technological purposes.

At 1212, it is determined (e.g., by controller component 302) whether new control data has been generated. For example, it can be determined whether new control data is generated for the one or more devices. If yes, the methodology 1200 returns to 1210 to provide the new control data to the one or more devices. If no, the methodology 1200 can end.

Figure 13:
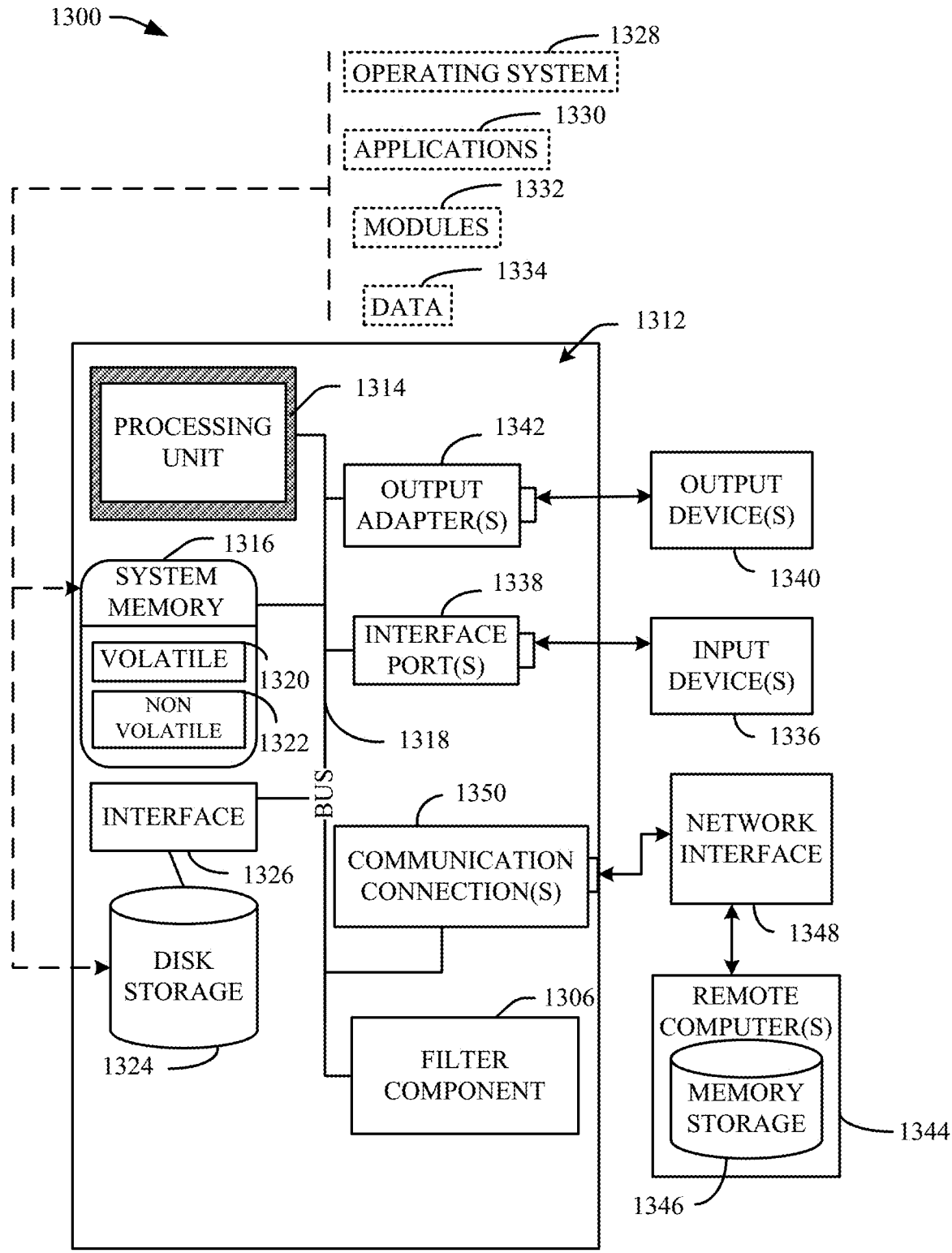
FIG. 13 is a schematic block diagram illustrating a suitable operating environment.
Figure 14:
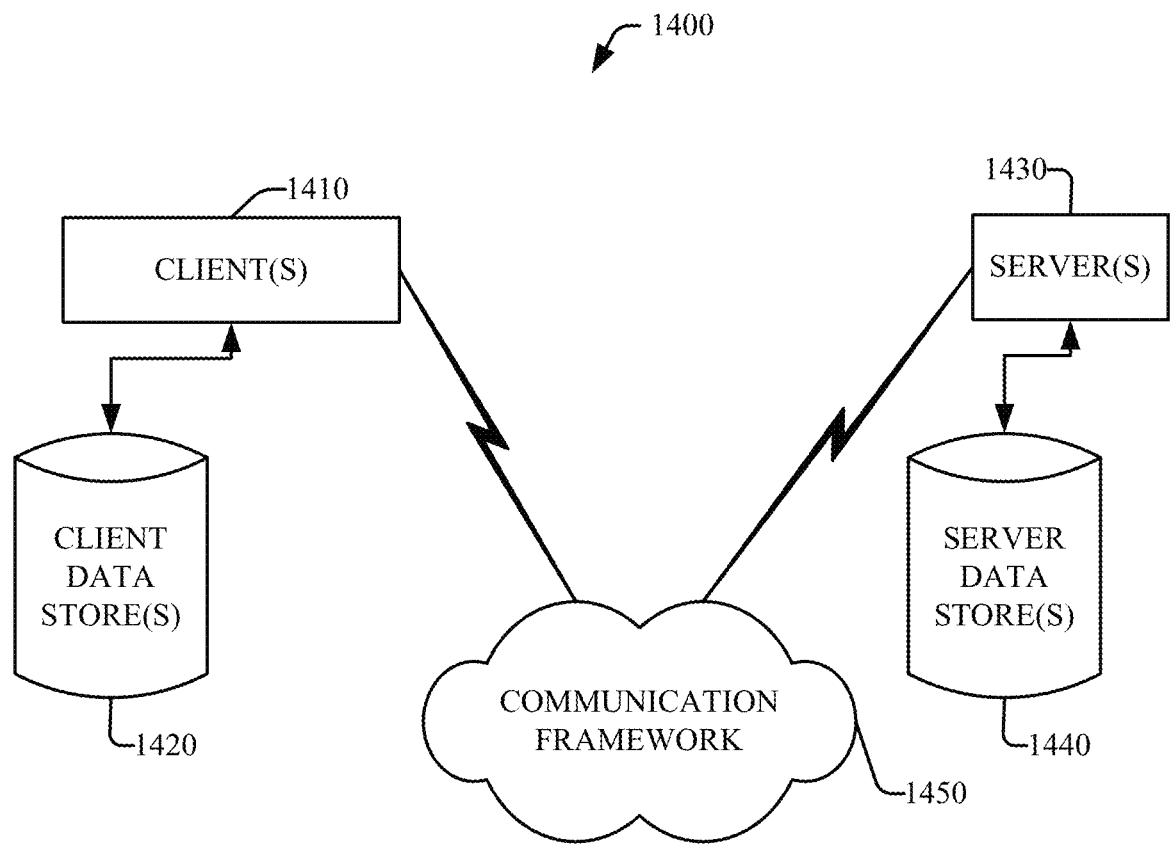
FIG. 14 is a schematic block diagram of a sample-computing environment.

In order to provide a context for the various aspects of the disclosed subject matter, FIGS. 13 and 14 as well as the following discussion are intended to provide a brief, general description of a suitable environment in which the various aspects of the disclosed subject matter may be implemented.

With reference to FIG. 13, a suitable environment 1300 for implementing various aspects of this disclosure includes a computer 1312. The computer 1312 includes a processing unit 1314, a system memory 1316, and a system bus 1318. The system bus 1318 couples system components including, but not limited to, the system memory 1316 to the processing unit 1314. The processing unit 1314 can be any of various available processors. Dual microprocessors and other multiprocessor architectures also can be employed as the processing unit 1314.

The system bus 1318 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1316 includes volatile memory 1320 and nonvolatile memory 1322. The basic input/output system (BIOS), containing the basic routines to transfer information between elements within the computer 1312, such as during start-up, is stored in nonvolatile memory 1322. By way of illustration, and not limitation, nonvolatile memory 1322 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1320 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1312 also includes removable/non-removable, volatile/non-volatile computer storage media. FIG. 13 illustrates, for example, a disk storage 1324. Disk storage 1324 includes, but is not limited to, devices like a magnetic disk drive, floppy disk drive, tape drive, Jaz drive, Zip drive, LS-100 drive, flash memory card, or memory stick. The disk storage 1324 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1324 to the system bus 1318, a removable or non-removable interface is typically used, such as interface 1326.

FIG. 13 also depicts software that acts as an intermediary between users and the basic computer resources described in the suitable operating environment 1300. Such software includes, for example, an operating system 1328. Operating system 1328, which can be stored on disk storage 1324, acts to control and allocate resources of the computer system 1312. System applications 1330 take advantage of the management of resources by operating system 1328 through program modules 1332 and program data 1334, e.g., stored either in system memory 1316 or on disk storage 1324. It is to be appreciated that this disclosure can be implemented with various operating systems or combinations of operating systems.

A user enters commands or information into the computer 1312 through input device(s) 1336. Input devices 1336 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1314 through the system bus 1318 via interface port(s) 1338. Interface port(s) 1338 include, for example, a serial port, a parallel port, a game port, and a universal serial bus (USB). Output device(s) 1340 use some of the same type of ports as input device(s) 1336. Thus, for example, a USB port may be used to provide input to computer 1312, and to output information from computer 1312 to an output device 1340. Output adapter 1342 is provided to illustrate that there are some output devices 1340 like monitors, speakers, and printers, among other output devices 1340, which require special adapters. The output adapters 1342 include, by way of illustration and not limitation, video and sound cards that provide a means of connection between the output device 1340 and the system bus 1318. It should be noted that other devices and/or systems of devices provide both input and output capabilities such as remote computer(s) 1344.

Computer 1312 can operate in a networked environment using logical connections to one or more remote computers, such as remote computer(s) 1344. The remote computer(s) 1344 can be a personal computer, a server, a router, a network PC, a workstation, a microprocessor based appliance, a peer device or other common network node and the like, and typically includes many or all of the elements described relative to computer 1312. For purposes of brevity, only a memory storage device 1346 is illustrated with remote computer(s) 1344. Remote computer(s) 1344 is logically connected to computer 1312 through a network interface 1348 and then physically connected via communication connection 1350. Network interface 1348 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1350 refers to the hardware/software employed to connect the network interface 1348 to the bus 1318. While communication connection 1350 is shown for illustrative clarity inside computer 1312, it can also be external to computer 1312. The hardware/software necessary for connection to the network interface 1348 includes, for exemplary purposes only, internal and external technologies such as, modems including regular telephone grade modems, cable modems and DSL modems, ISDN adapters, and Ethernet cards.

FIG. 14 is a schematic block diagram of a sample-computing environment 1400 with which the subject matter of this disclosure can interact. The system 1400 includes one or more client(s) 1410. The client(s) 1410 can be hardware and/or software (e.g., threads, processes, computing devices). The system 1400 also includes one or more server(s) 1430. Thus, system 1400 can correspond to a two-tier client server model or a multi-tier model (e.g., client, middle tier server, data server), amongst other models. The server(s) 1430 can also be hardware and/or software (e.g., threads, processes, computing devices). The servers 1430 can house threads to perform transformations by employing this disclosure, for example. One possible communication between a client 1410 and a server 1430 may be in the form of a data packet transmitted between two or more computer processes.

The system 1400 includes a communication framework 1450 that can be employed to facilitate communications between the client(s) 1410 and the server(s) 1430. The client(s) 1410 are operatively connected to one or more client data store(s) 1420 that can be employed to store information local to the client(s) 1410. Similarly, the server(s) 1430 are operatively connected to one or more server data store(s) 1440 that can be employed to store information local to the servers 1430.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:
   modeling circuitry configured to generate a three-dimensional model of a mechanical device based on a library of stored data elements, wherein the data elements each comprise one or more properties of the mechanical device, and wherein generating a three-dimensional model further comprises determining a set of one or more control volumes associated with the mechanical device, the set of one or more control volumes abstracting a region of the mechanical device through which a fluid and/or an electrical current flows;
   machine learning circuitry configured to perform a machine learning process associated with the three-dimensional model and predict one or more characteristics of the mechanical device based on the machine learning process;

three-dimensional design circuitry configured to provide a three-dimensional design environment associated with the three-dimensional model, wherein the three-dimensional design environment renders physics modeling data of the mechanical device on the three-dimensional model based on the one or more characteristics of the mechanical device; and data collection circuitry configured to collect machine data from each of a plurality of additional mechanical devices, wherein the data collection circuitry is configured to collect the machine data via a network device of a communication network, and wherein the machine learning circuitry is configured to update the three-dimensional model associated with the three-dimensional design environment, including the set of one or more control volumes, based on an aggregation of the machine data collected from the plurality of additional mechanical devices, wherein the plurality of additional mechanical devices and the mechanical device are each a same type of mechanical device.

2. The system of claim 1, wherein the data collection circuitry is configured to receive the machine data from one or more sensor devices associated with respective ones of the additional mechanical devices, wherein the one or more sensor devices are in communication with the system via the network device.

3. The system of claim 1, wherein the machine learning process is a first machine learning process, and wherein the machine learning circuitry is configured to perform a second machine learning process based on the machine data.

4. The system of claim 3, wherein the modeling circuitry is configured to generate a modified version of the three-dimensional model based on the second machine learning process.

5. The system of claim 1, wherein the machine data is real-time data collected, by the data collection circuitry, approximately in real-time from one or more sensor devices in communication with the system via the network device.

6. The system of claim 1, further comprising:
controller circuitry configured to generate, for a device in communication with the system via the network device, control data to control one or more operations of the mechanical device based on the three-dimensional model.

7. The system of claim 6, wherein the mechanical device is the mechanical device associated with the three-dimensional model, and wherein the controller circuitry is configured to generate, for the mechanical device, the control data to control one or more operations of the mechanical device.

8. The system of claim 6, wherein the control data comprises maintenance data indicative of maintenance information for the mechanical device, wherein the controller circuitry is configured to transmit the maintenance data to the mechanical device to control one or more operations related to maintenance for the mechanical device.

9. The system of claim 1, wherein the machine learning circuitry is configured to perform the machine learning process based on input data indicative of input received from the mechanical device and the plurality of additional mechanical devices, and wherein the three-dimensional design environment renders the physics modeling data of the mechanical device on the three-dimensional model based on the input data and the one or more characteristics of the mechanical device.

10. The system of claim 1, wherein the machine learning circuitry is configured to perform the machine learning process based on fluid data indicative of a fluid received by the mechanical device, and wherein the three-dimensional design environment renders the physics modeling data of the mechanical device based on the fluid data and the one or more characteristics of the mechanical device on the three-dimensional model.

11. A method, comprising:
generating, by a system comprising a processor, a three-dimensional model of a mechanical device based on a library of stored data elements, wherein the data elements each comprise one or more properties of the mechanical device, and wherein generating a three-dimensional model further comprises determining a set of one or more control volumes associated with the mechanical device, the set of one or more control volumes abstracting a region of the mechanical device through which a fluid and/or an electrical current flows;

predicting, by the system, fluid flow and physics behavior associated with the three-dimensional model based on a machine learning process associated with the three-dimensional model;

rendering, by the system, physics modeling data of the mechanical device within a three-dimensional design environment based on the fluid flow and the physics behavior;

receiving, by the system, machine data from each of a plurality of additional mechanical devices, wherein the machine data is received via a network device of a communication network; and updating, by the system, the physics modeling data and the set of one or more control volumes within the three-dimensional design environment based on an aggregation of the machine data collected from the plurality of additional mechanical devices, wherein the plurality of additional mechanical devices and the mechanical device are each a same type of mechanical device.

12. The method of claim 11, wherein the machine learning process is a first machine learning process, and wherein the updating comprises performing a second machine learning process based on the machine data to generate updated physics modeling data.

13. The method of claim 12, further comprising:
rendering, by the system, the updated physics modeling data within the three-dimensional design environment.

14. The method of claim 12, further comprising: generating, by the system, control data to control one or more operations of a device based on the physics modeling data; and
transmitting, by the system, the control data to the mechanical device.

15. The method of claim 11, wherein the receiving the machine data comprises receiving the machine data from one or more sensor devices operatively connected to respective ones of the additional mechanical devices, and wherein the one or more sensor devices are in communication with the system via the network device.

16. The method of claim 11, wherein the receiving the machine data comprises receiving real-time data approximately in real-time from one or more sensor devices in communication with the system via the network device.

17. A non-transitory computer readable device comprising instructions that, in response to execution, cause a system comprising a processor to perform operations, comprising:

generating a three-dimensional model of a mechanical device based on a library of stored data elements, wherein the data elements each comprise one or more properties of the mechanical device, and wherein generating a three-dimensional model further comprises determining a set of one or more control volumes associated with the mechanical device, the set of one or more control volumes abstracting a region of the mechanical device through which a fluid and/or an electrical current flows;

performing a first machine learning process associated with the three-dimensional model to predict one or more characteristics of the mechanical device;

generating physics modeling data for the mechanical device based on the first machine learning process;

receiving, from a network device of a communication network, machine data from each of a plurality of additional mechanical devices;

updating the physics modeling data to generate updated physics modeling data and the set of one or more control for the mechanical device based on a second machine learning process and based on an aggregation of the machine data collected from the plurality of additional mechanical devices, wherein the plurality of additional mechanical devices and the mechanical device are each a same type of mechanical device; and providing a three-dimensional design environment associated with the three-dimensional model that renders the updated physics modeling data for the mechanical device.

18. The non-transitory computer readable device of claim 17, wherein the receiving the machine data comprises receiving real-time data approximately in real-time from one or more sensor devices via the network device.

19. The non-transitory computer readable device of claim 17, wherein the operations further comprise:
generating control data to control one or more operations of the mechanical device based on the physics modeling data.

20. The non-transitory computer readable device of claim 19, wherein the operations further comprise:
transmitting the control data to the mechanical device to facilitate performance of the one or more operations by the mechanical device.

* * * * *